United States Patent
Mou et al.

(10) Patent No.: US 10,935,532 B2
(45) Date of Patent: *Mar. 2, 2021

(54) ACTUATION-AND-DETECTING MODULE

(71) Applicant: Microjet Technology Co., Ltd., Hsinchu (TW)

(72) Inventors: Hao-Jan Mou, Hsinchu (TW); Ching-Sung Lin, Hsinchu (TW); Yung-Lung Han, Hsinchu (TW); Chi-Feng Huang, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 164 days.

This patent is subject to a terminal disclaimer.

(21) Appl. No.: 16/255,484

(22) Filed: Jan. 23, 2019

(65) Prior Publication Data
US 2019/0302075 A1      Oct. 3, 2019

(30) Foreign Application Priority Data
Mar. 30, 2018   (TW) .................................. 107111390

(51) Int. Cl.
*G01N 33/00*   (2006.01)
*G01N 15/06*   (2006.01)
(Continued)

(52) U.S. Cl.
CPC ....... *G01N 33/0036* (2013.01); *F04B 43/046* (2013.01); *G01N 1/22* (2013.01);
(Continued)

(58) Field of Classification Search
CPC ...... G01N 33/0036; G01N 1/22; F04B 43/046
See application file for complete search history.

(56) References Cited

U.S. PATENT DOCUMENTS 9,875,631 B2 *   1/2018   Mittleman ............. G08B 17/00
2015/0338390 A1   11/2015   Anglin, Jr. et al.
(Continued)

FOREIGN PATENT DOCUMENTS

CN      1157601 C     7/2004
EP      2620768 A1    7/2013
(Continued)

*Primary Examiner* — Jamel E Williams
(74) *Attorney, Agent, or Firm* — Birch, Stewart, Kolasch & Birch, LLP

(57) ABSTRACT

An actuation-and-detecting module is disclosed and includes a main body, a particle detecting base, plural actuators and sensors. The main body has a first compartment divided into a first chamber and a second chamber, a second compartment having a third chamber and a third compartment divided into a fourth chamber and a fifth chamber by a carrying partition. The particle detecting base is disposed between the fourth chamber and the carrying partition. The first actuator is disposed between the second chamber and a first partition. The second actuator is disposed within a receiving slot of the particle detecting base. The first sensor is disposed within the first chamber. The second sensor is disposed within the third chamber for detecting the air in the third chamber. The third sensor is disposed within a detecting channel of the particle detecting base for detecting the air in the detecting channel.

20 Claims, 21 Drawing Sheets

(51) Int. Cl.
*G01N 1/22* (2006.01)
*H04M 1/02* (2006.01)
*F04B 43/04* (2006.01)

(52) U.S. Cl.
CPC .......... *G01N 1/2273* (2013.01); *G01N 15/06* (2013.01); *G01N 33/0009* (2013.01); *H04M 1/026* (2013.01); *H04M 2250/12* (2013.01)

(56) References Cited

U.S. PATENT DOCUMENTS

2017/0138834 A1    5/2017  Krauss
2019/0302076 A1*  10/2019  Mou ................... F04B 43/046

FOREIGN PATENT DOCUMENTS

| EP | 2733484 A1 | 5/2014 |
| EP | 2905673 A2 | 8/2015 |
| EP | 3203079 A1 | 8/2017 |
| JP | 5692465 B2 | 4/2015 |
| TW | M553862 U | 1/2018 |

* cited by examiner

ACTUATION-AND-DETECTING MODULE

FIELD OF THE DISCLOSURE

The present disclosure relates to an actuation-and-detecting module, and more particularly to an actuation-and-detecting module applied to a thin portable device for monitoring air quality.

BACKGROUND OF THE DISCLOSURE

Nowadays, people are paying more and more attention to the air quality in the environment. For example, it is important to monitor carbon monoxide, carbon dioxide, volatile organic compounds (VOC), Particulate Matter (PM2.5), nitrogen monoxide, sulfur monoxide, and so on. The exposures of these substances in the environment will cause human health problems or even threaten the human life. Therefore, it is important for every country to monitor the air quality in the environment.

Generally, it is feasible to use a gas sensor to monitor the air quality in the environment. If the gas sensor is capable of immediately providing people with the monitored information relating to the environment for caution, it may help people escape or prevent from the injuries and influence on human health caused by the exposure of the substances described above in the environment. In other words, the gas sensor is suitably used for monitoring the ambient air in the environment.

The conventional gas sensor performs detecting and monitoring based on the air introduced to the surface of the gas sensor by the ambient airflow. If there is no actuator for guiding the air and increasing the flow rate of the air, it should take long time to transport the air to the gas sensor, and thus the detecting efficiency is not good. However, if an actuator is added to form an actuation-and-detecting module in combination, the actions of the actuator will generate heat caused by continuous vibration at high speed, and the heat will be transferred to the periphery of the gas sensor. In that, the heat further causes a temperature difference between the air surrounding the periphery of the gas sensor and the ambient air surrounding the actuation-and-detecting module, and the monitoring results of the gas sensor is influenced. In addition, in case that the actuation-and-detecting module is applied to a device (such as a portable electronic device) in combination, the electronic components (such as the circuit board and the processor) in the interior of the device will generate some gas pollution, heat source and other interfering substances after operation. When the interfering substances are introduced into the actuation-and-detecting module to mix with the air to be sensed, the monitoring quality of the gas sensor is influenced. The gas sensor fails to measure the true characteristics and composition of the air surrounding the actuation-and-detecting module. It results in errors in the measurement results.

Therefore, there is need to provide an actuation-and-detecting module to achieve the purposes of improving the detecting efficiency, measuring the target gas with precision, and eliminating the other factors to influence the gas sensor, which is an urgent need for the industry to solve.

SUMMARY OF THE DISCLOSURE

An object of the present disclosure is to provide an actuation-and-detecting module applied to a thin portable device in combination for monitoring the air quality. The actuation-and-detecting module includes a main body, an actuator and a gas sensor. With the arrangement of the actuator, the gas can be introduced to the surface of the gas sensor rapidly for measurement, so as to improve the detecting efficiency of the gas sensor. The main body has a detecting chamber. The detecting chamber has two openings, one for inhaling the air and the other one for discharging the air. The air inhaled in the detecting chamber does not flow back along the same path to be discharged from the same opening. That is, the detecting chamber provides space for measuring the air flowing in one way direction. In the detecting chamber, a resonance plate is driven by the piezoelectric actuator, and the actuation-and-detecting module can introduce the air from the outside of the thin portable device for measurement. Owing to the design of the present disclosure, the properties of the air to be measured in the actuation-and-detecting module are the same as the properties of the ambient air outside the thin portable device.

In accordance with an aspect of the present disclosure, there is provided an actuation-and-detecting module. The actuation-and-detecting module includes a main body, a fine particle detecting base, a plurality of actuators and a plurality of sensors. The main body includes a plurality of compartments and the plurality of compartments includes a first compartment, a second compartment and a third compartment. The first compartment includes a first chamber, a second chamber, a first partition, a first inlet and a first outlet. The first chamber and the second chamber are divided through the first partition, the first inlet is in fluid communication with the first chamber. The first outlet is in fluid communication with the second chamber. The first partition has a first communication opening in fluid communication with the first chamber and the second chamber. The second compartment is integrally combined with the first compartment and includes a third chamber and a gas through hole, wherein the gas through hole is in fluid communication with the third chamber. The third compartment is integrally combined with the first compartment and the second compartment and includes a fourth chamber, a fifth chamber, a carrying partition, a second inlet and a second outlet. The fourth chamber and the fifth chamber are divided through the carrying partition. The second inlet is in fluid communication with the fourth chamber. The second outlet is in fluid communication with the fifth chamber. The carrying partition has a second communication opening in fluid communication with the fourth chamber and the fifth chamber. The fine particle detecting base is disposed between the fourth chamber and the carrying partition and has a detecting channel and a receiving slot. The receiving slot is disposed in one end of the detecting channel and in fluid communication with the detecting channel. The plurality of actuators include a first actuator and a second actuator. The first actuator is disposed between the second chamber and the first partition to allow air to flow into the first chamber through the first inlet, be transported to the second chamber through the first communication opening and be discharged out through the first outlet, so as to achieve air transportation of the first compartment in one way. The second actuator is disposed within the receiving slot of the fine particle detecting base and seals one end of the detecting channel to allow air to flow into the fourth chamber through the second inlet, be transported to the fifth chamber through the second communication opening and be discharge out through the second outlet, so as to achieve air transportation of the third compartment in one way. The plurality of sensors include a first sensor, a second sensor and a third sensor. The first sensor is disposed within the first chamber and spaced apart from the first actuator to detect the air flowing through a surface thereof The second sensor is disposed within the third chamber to detect the air flowing into the third chamber. The third sensor is disposed on the carrying partition and located within the detecting channel of the fine particle detecting base to detect the air flowing into the detecting channel.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this disclosure are presented herein for purpose of illustration and description only. It is not intended to be exhaustive or to be limited to the precise form disclosed.

Figure 1:
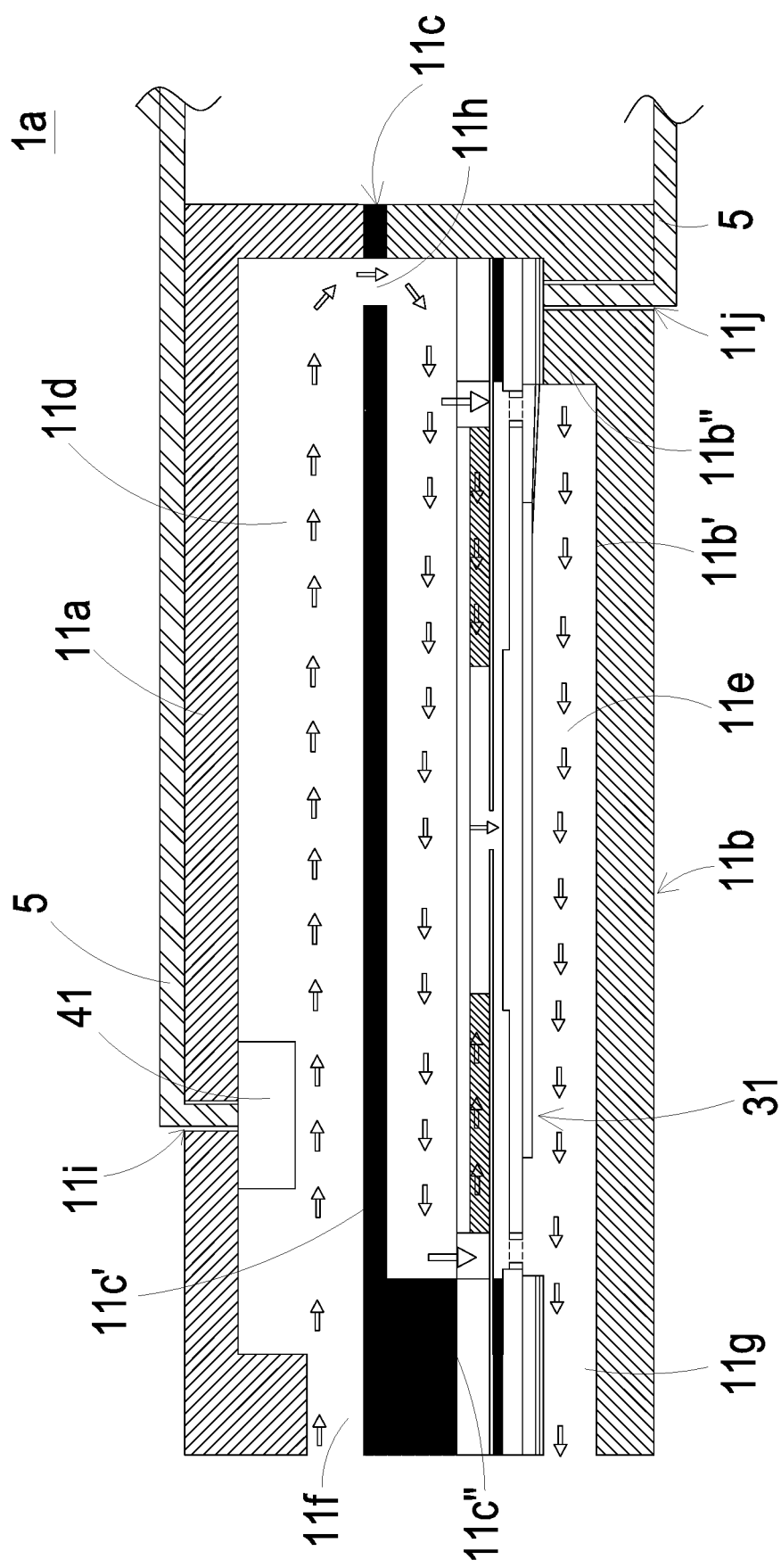
FIG. 1 is a schematic cross-sectional view illustrating a first compartment of an actuation-and-detecting module according to an embodiment of the present disclosure.
Figure 4:
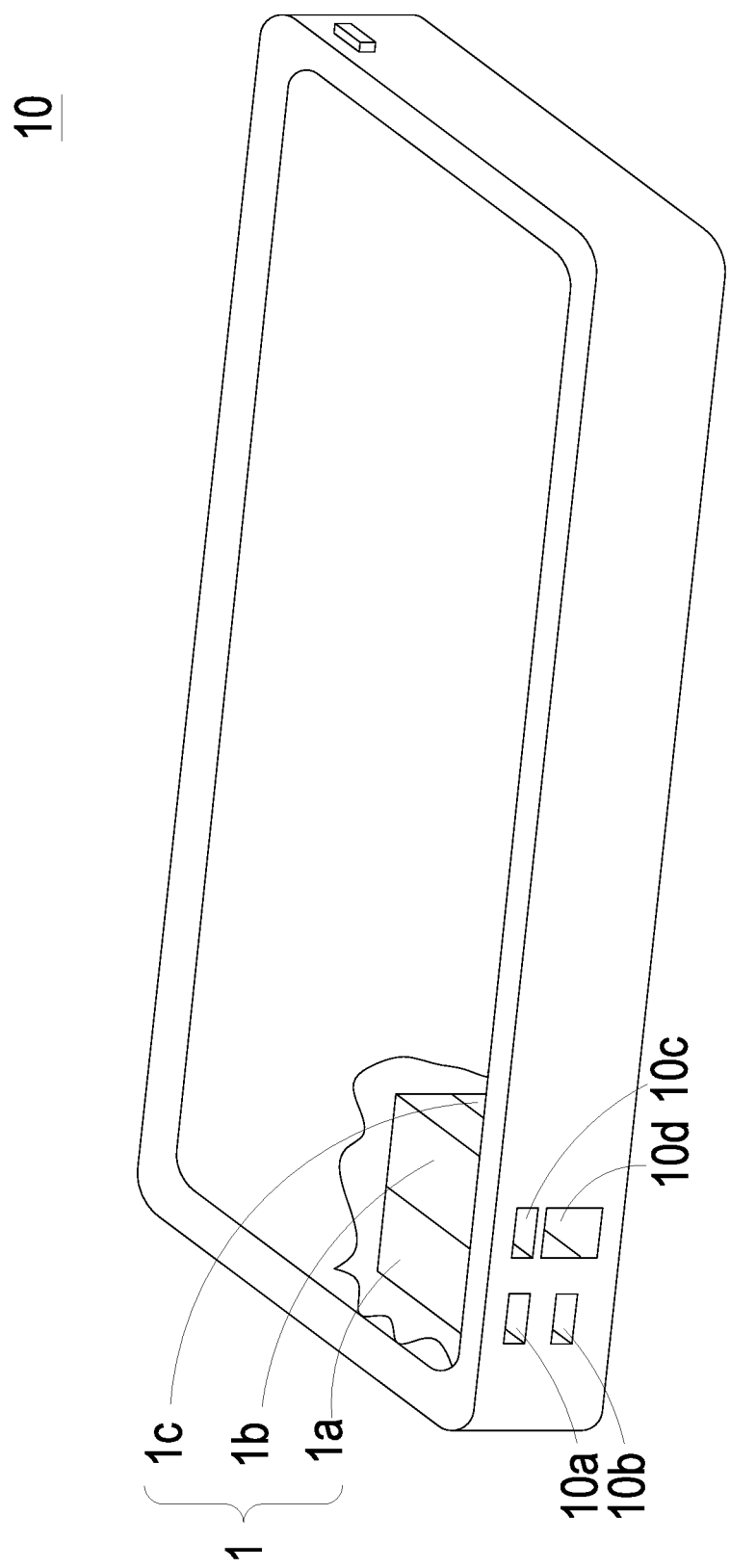
FIG. 4 is schematic view illustrating the actuation-and-detecting module applied to a thin portable device according to the an embodiment of the present disclosure.
Figure 6:
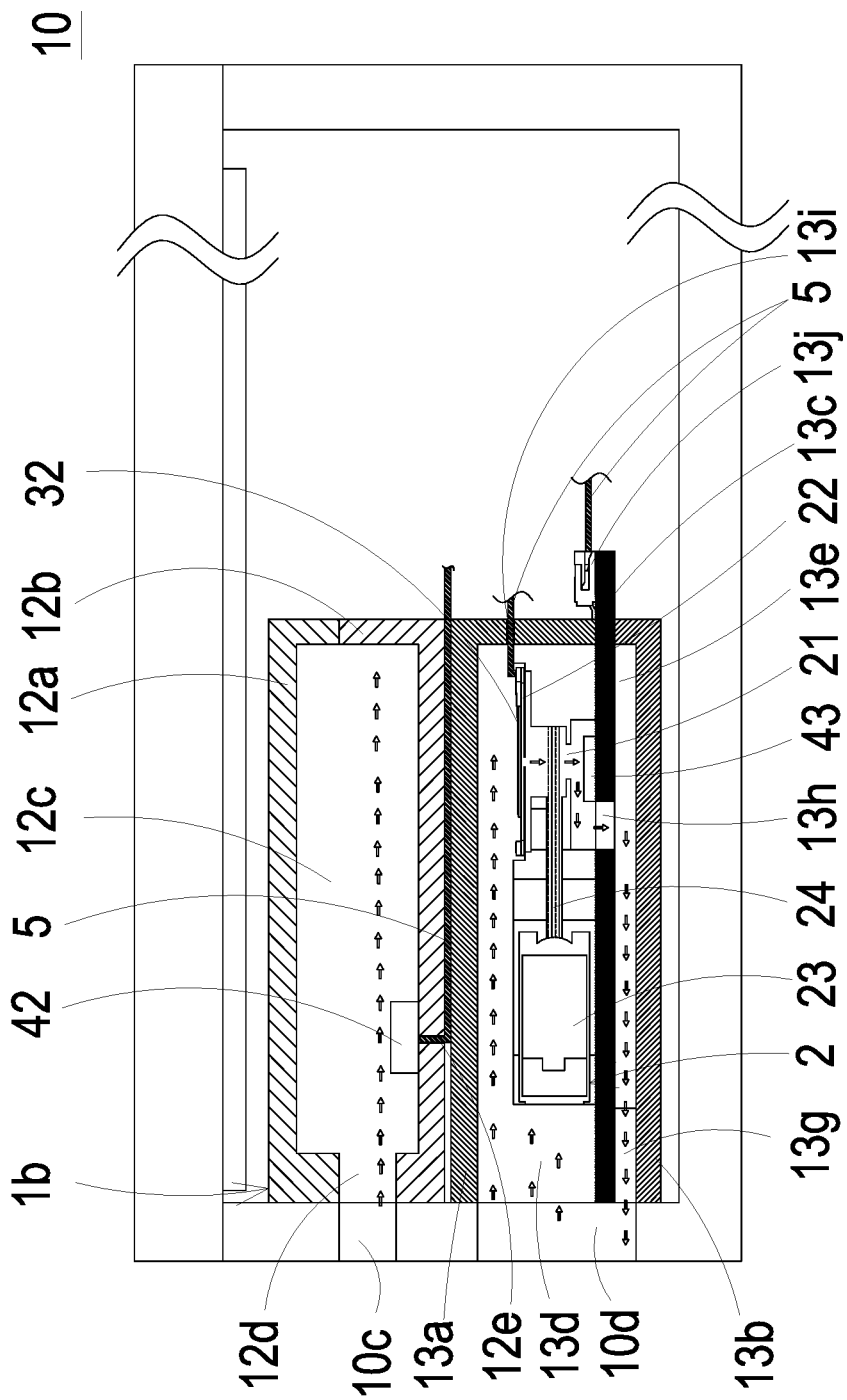
FIG. 6 is a schematic cross-sectional view illustrating a second compartment and the third compartment of the actuation-and-detecting module applied to the thin portable device of FIG. 4.
Figure 7A:
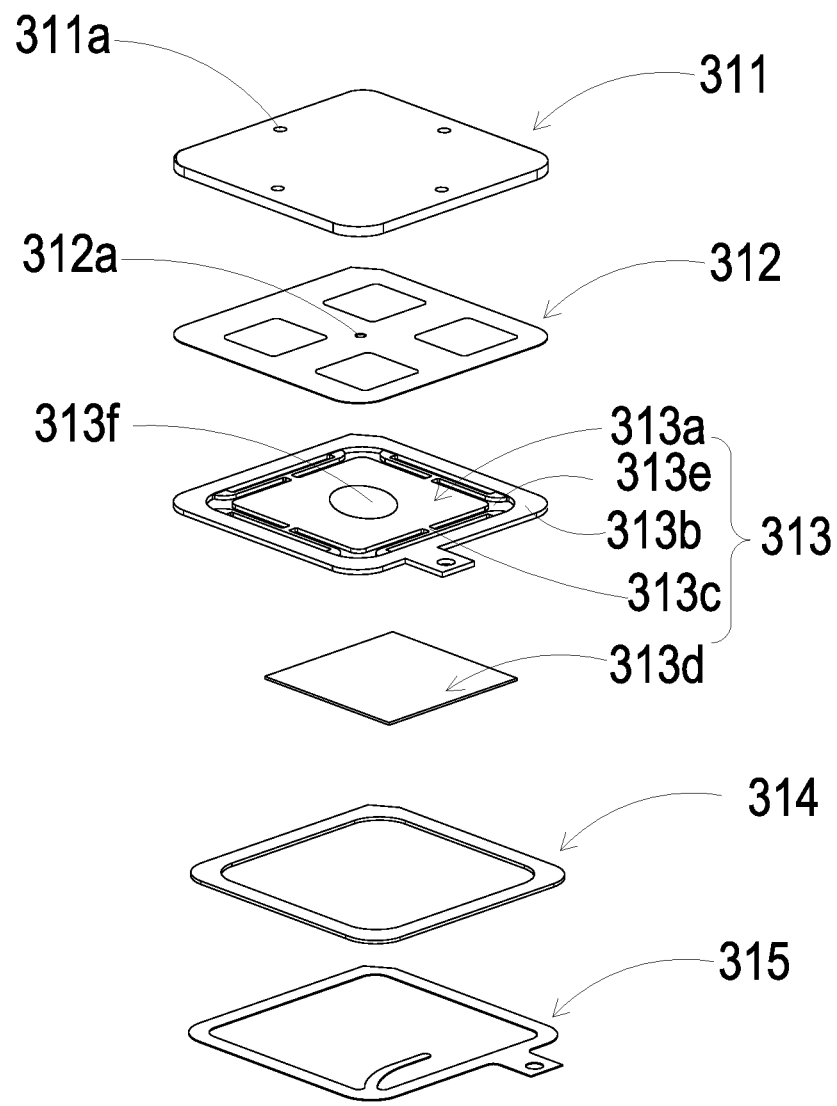
FIG. 7A is an exploded view illustrating a first actuator of the actuation-and-detecting module according to an embodiment of the present disclosure and taken from top side.
Figure 7B:
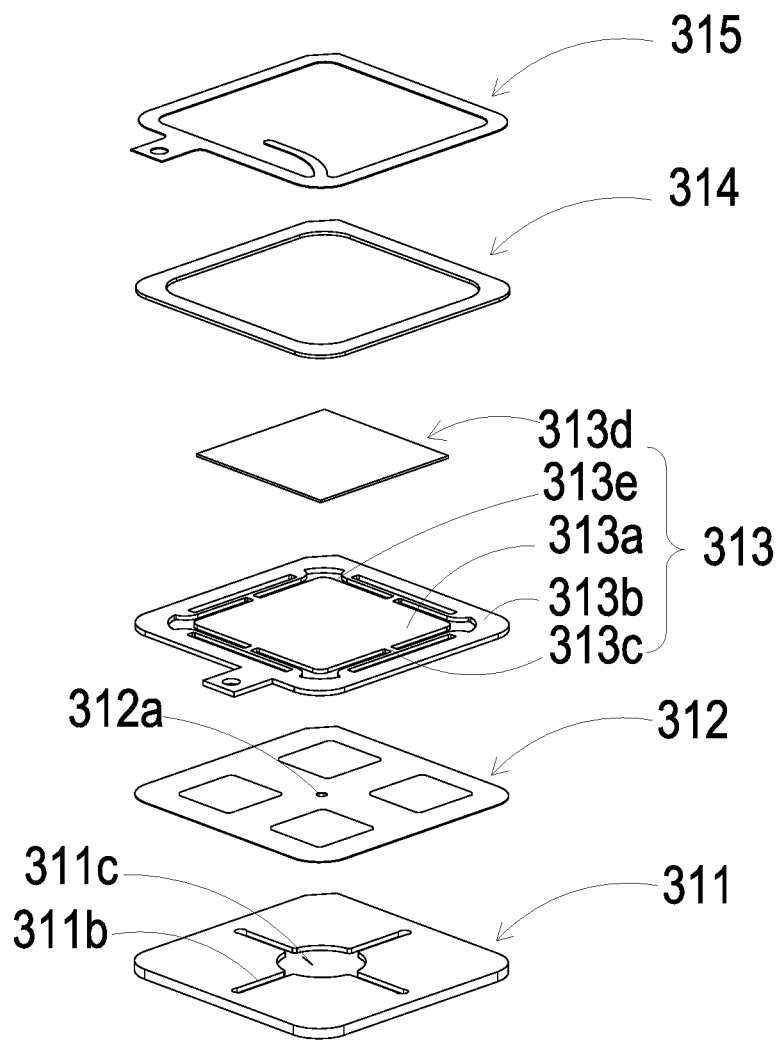
FIG. 7B is an exploded view illustrating the first actuator of the actuation-and-detecting module according to the embodiment of the present disclosure and taken from bottom side.

Please refer to FIGS. 1, 4 and 6. The present disclosure provides an actuation-and-detecting module including at least one main body 1, at least one fine particle detecting base 2, a plurality of actuators, a plurality of sensors, at least one first compartment 1a, at least one second compartment 1b, at least one third compartment 1c, at least one first partition 11c, at least one first chamber 11d, at least one second chamber 11e, at least one first inlet 11f, at least one first outlet 11g, at least one first communication opening 11h, at least one third chamber 12c, at least one carrying partition 13c, at least one fourth chamber 13d, at least one fifth chamber 13e, at least one second inlet 13f, at least one second outlet 13g, at least one second communication opening 13h, at least one detecting channel 21, at least one receiving slot 22, at least one first actuator 31, at least one second actuator 32, at least one first sensor 41, at least one second sensor 42, at least one third sensor 43 and at least one gas through hole 12d. The numbers of the main body 1, the fine particle detecting base 2, the first compartment 1a, the second compartment 1b, the third compartment 1c, the first partition 11c, the first chamber 11d, the second chamber 11e, the first inlet 11f, the first outlet 11g, the first communication opening 11h, the third chamber 12c, the carrying partition 13c, the fourth chamber 13d, the fifth chamber 13e, the second inlet 13f, the second outlet 13g, the second communication opening 13h, the detecting channel 21, the receiving slot 22, the first actuator 31, the second actuator 32, the first sensor 41, the second sensor 42, the third sensor 43 and the gas through hole 12d are exemplified by one for each respectively in the following embodiments but not limited thereto. It is noted that each of the main body 1, the fine particle detecting base 2, the first compartment 1a, the second compartment 1b, the third compartment 1c, the first partition 11c, the first chamber 11d, the second chamber 11e, the first inlet 11f, the first outlet 11g, the first communication opening 11h, the third chamber 12c, the carrying partition 13c, the fourth chamber 13d, the fifth chamber 13e, the second inlet 13f, the second outlet 13g, the second communication opening 13h, the detecting channel 21, the receiving slot 22, the first actuator 31, the second actuator 32, the first sensor 41, the second sensor 42, the third sensor 43 and the gas through hole 12d can also be provided in plural numbers.

Figure 5:
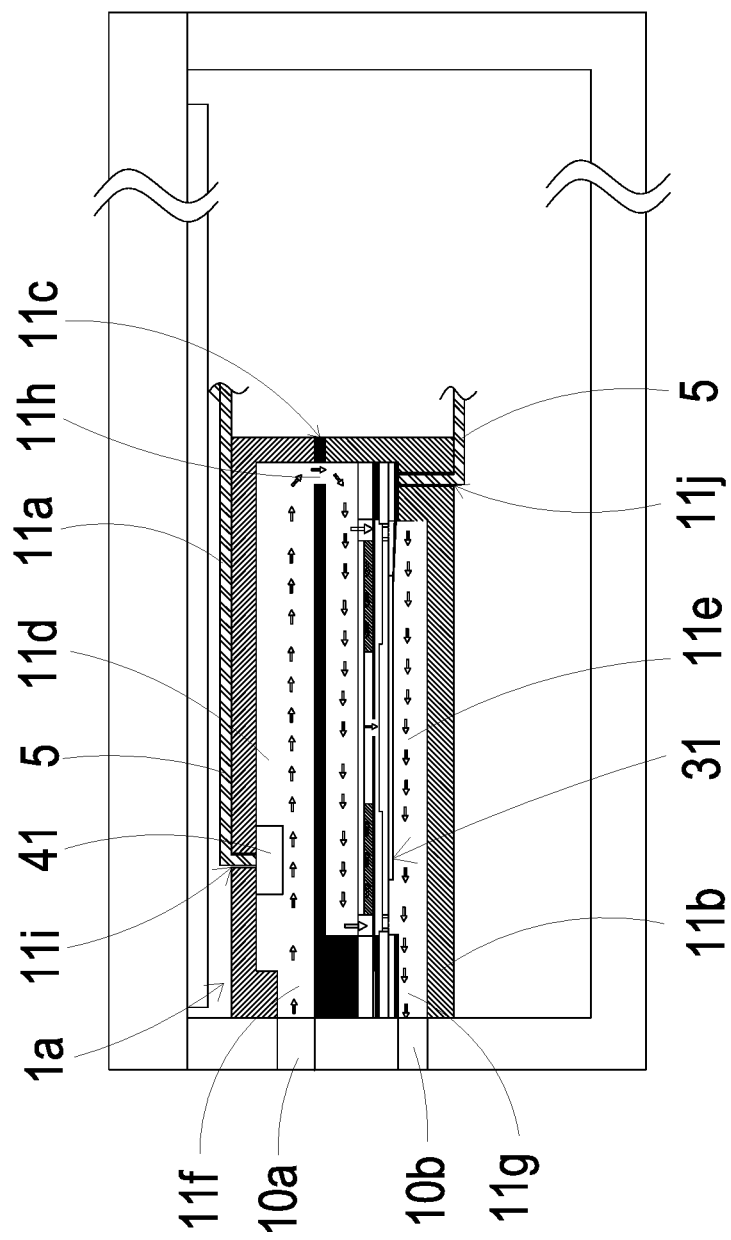
FIG. 5 is a schematic cross-sectional view illustrating a first compartment of the actuation-and-detecting module applied to the thin portable device of FIG. 4.

The present disclosure provides an actuation-and-detecting module. Please refer to FIGS. 1 to 6. The actuation-anddetecting module includes a main body 1, a fine particle detecting base 2, a plurality of actuators and a plurality of sensors. Please refer to FIGS. 4 to 6, firstly. The main body 1 includes a plurality of compartments, and the plurality of compartments include a first compartment 1a, a second compartment 1b and a third compartment 1c. The second compartment 1b is integrally combined with the first compartment 1a, and the third compartment 1c is integrally combined with the first compartment 1a and the second compartment 1b. The first compartment 1a has a sidewall abuts the second compartment 1b and the third compartment 1c. The second compartment 1b has a sidewall and a bottom surface adjoining the sidewall perpendicularly. The sidewall of the second compartment 1b is parallel to and abuts the sidewall of the first compartment 1a. The third compartment 1c has a sidewall and a top surface adjoining the sidewall perpendicularly. The sidewall of the third compartment 1c is parallel to and abuts the sidewall of the first compartment 1a. The top surface of the third compartment 1c is parallel to and abuts the bottom surface of the second compartment 1b. The first compartment 1a, the second compartment 1b, and the third compartment 1c are integrally combined as a whole, that is, the main body 1. The plurality of actuators includes a first actuator 31 and a second actuator 32. The plurality of sensors includes a first sensor 41, a second sensor 42 and a third sensor 43.

Please refer to FIG. 1, again. In the embodiment, the first compartment 1a includes a first sub-body 11a, a second sub-body 11b and a first partition 11c. The first sub-body 11a and the second sub-body 11b are connected to each other, and the first partition 11c is disposed between the first sub-body 11a and the second sub-body 11b, so that the inner space enclosed by the first sub-body 11a and the second sub-body 11b is divided into a first chamber 11d and a second chamber 11e by the first partition 11c. The inner space enclosed by the first sub-body 11a and the second sub-body 11b remains an opening in communication with an environment outside the first compartment 1a. Because of the first partition 11c, the opening is also divided into a first inlet 11f and a first outlet 11g. The first inlet 11f is disposed between the first sub-body 11a and the first partition 11c. The first inlet 11f is in fluid communication with the first chamber 11d. The first outlet 11g is disposed between the second sub-body 11b and the first partition 11c. The first outlet 11g is in fluid communication with the second chamber 11e. Both of the first inlet 11f and the first outlet 11g are disposed on the same side of the first compartment 1a. In addition, the first partition 11 has a first communication opening 11h in fluid communication with the first chamber 11d and second chamber 11e. Consequently, the first inlet 11f, the first chamber 11d, the first communication opening 11h, the second chamber 11e and the first outlet 11g form an airflow channel (as the path in the direction indicated by the arrows in FIG. 1) in the interior of the main body 1 for air transportation in one way. Rather than being inhaled and discharged by the same opening, the air is inhaled from the first inlet 11f, flows along the airflow channel, and then is discharged through the first outlet 11g into the environment. The first actuator 31 is disposed between the second sub-body 11b and the first partition 11c. In the embodiment, the first actuator 31 is disposed between the second sub-body 11b and the first partition 11c and has one end fixed on the second sub-body 11b and another end fixed on the first partition 11c, so as to close the second chamber 11e. More specifically, one end of the first actuator 31 seals the edge of the second sub-body 11b, and another end of the first actuator 31 seals the edge of the first partition 11c. The second sub-body 11b has an inner surface 11b' and a protrusion portion 11b". The protrusion portion 11b" protrudes from the inner surface 11b' toward the first partition 11c. The first partition 11c has a surface 11c' parallel to the inner surface 11b', and has a protrusion portion 11c". The protrusion portion 11c" protrudes from the surface 11c' toward second sub-body 11b. The protrusion portion 11b" and the protrusion portion 11c" extend in opposite directions toward each other, thereby providing platforms for supporting the first actuator 31. Also, the design of the protrusion 11c" allows one part of the airflow channel in the second chamber 11e to be formed between the first actuator 31 and the first partition 11c, and the design of the protrusion portion 11b" allows another part of the airflow channel in the second chamber 11e to be formed between the first actuator 31 and the second sub-body 11b. The first actuator 31 seals the edge of the protrusion portion 11b" and the edge of the protrusion portion 11c". By driving the first actuator 31 to actuate the operation of air transportation, a negative pressure is formed in the first chamber 11d, and air is introduced into the first chamber 11d through the first inlet 11f, and then flows into the second chamber 11e through the first communication opening 11h. Moreover, by further driving the first actuator 31 to actuate the operation of air transportation, the air introduced into the second chamber 11e is discharged out from the first outlet 11g, so as to achieve air transportation in one way. The first sensor 41 is disposed in the first chamber 11d and is spaced apart from the first actuator 31. The first sensor 41 detects the air flowing through the surface thereof. In the embodiment, the first sensor 41 and the first actuator 31 are spaced apart through the first partition 11c. That is, the first partition 11c divides the inner space into two chambers, the first sensor 41 is disposed in the first chamber 11d and the first actuator 31 is disposed in the second chamber 11e, by which the first sensor 41 is spatially separated from the first actuator 31. As the first actuator 31 is driven to actuate the operation of air transportation, the continuous vibration at high speed will generate heat that may interfere with the first sensor 41. Under this circumstance, the first partition 11c can suppress the interference caused by the generated heat.

In the embodiment, the first sensor 41 can be for example a gas sensor, which is at least one selected from the group consisting of an oxygen sensor, a carbon monoxide sensor, a carbon dioxide sensor, a volatile organic compound sensor and combinations thereof. Alternatively, the gas sensor is at least one selected from the group consisting of a bacterium sensor, a virus sensor, a microorganism sensor and combinations thereof.

Please refer to FIG. 1 again. The first sub-body 11a of the first compartment 1a has a first connection through hole 11i to allow a flexible circuit board 5 to be inserted to connect to the first sensor 41. The first connection through hole 11i is sealed after connection so as to avoid the air to flow into the first chamber 11d therethrough. The second sub-body 11b has a second connection through 11j hole to allow a flexible circuit board 5 to be inserted to connect to the first actuator 31. The second connection through hole 11j is sealed after connection so as to avoid the air to flow into the second chamber 11e therethrough. Thus, the actuation-and-detecting module forms a detecting compartment having one-way openings to transport the air in one way for measurement.

Figure 2:
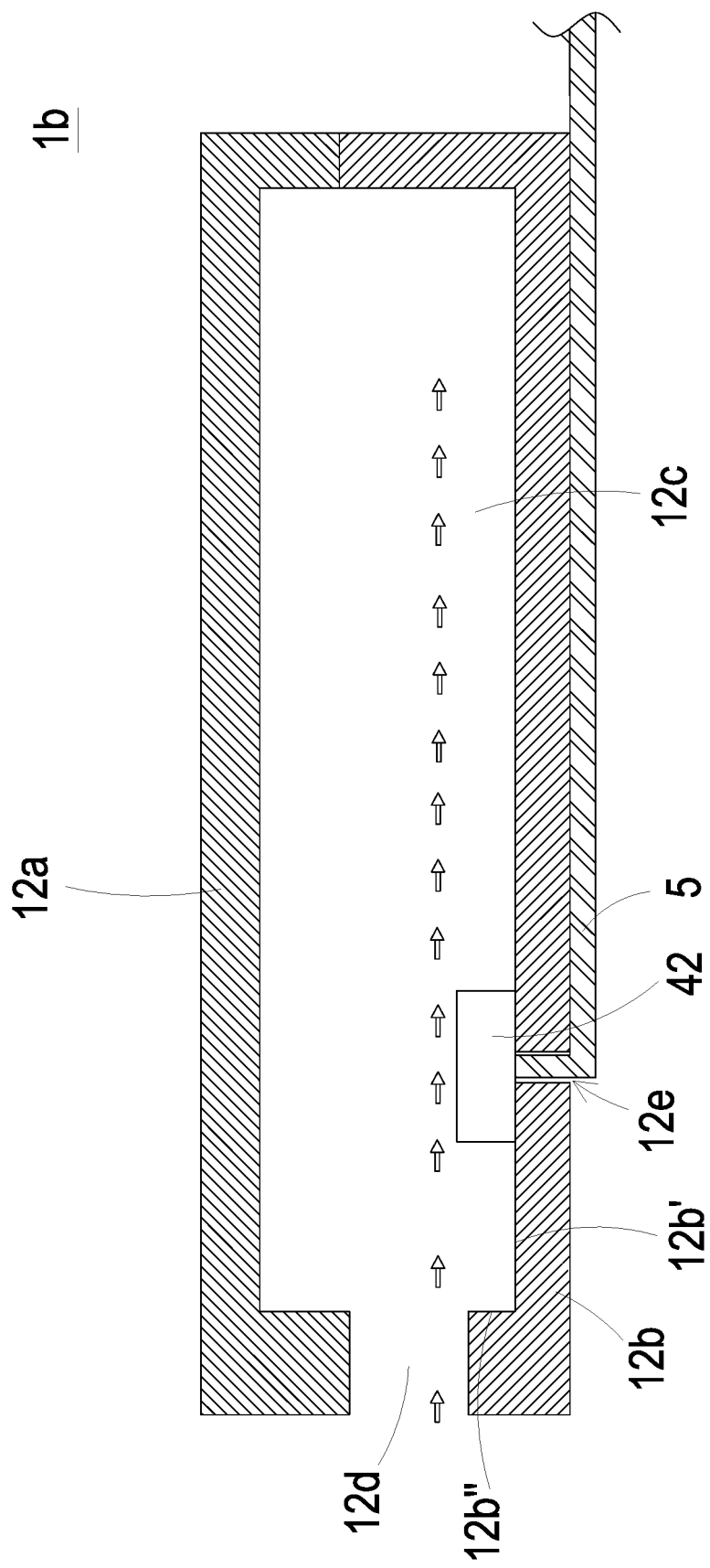
FIG. 2 is a schematic cross-sectional view illustrating a second compartment of the actuation-and-detecting module according to an embodiment of the present disclosure.

Please refer to FIG. 2. In the embodiment, the second compartment 1b includes a third sub-body 12a and a fourth sub-body 12b. The third sub-body 12a and the fourth sub-body 12b are connected to each other to define a third chamber 12c therebetween. A gas through hole 12d is formed at one end of the third sub-body 12a and the fourth sub-body 12b, and the gas through hole 12d is in fluid communication with the third chamber 12c. The fourth sub-body 12b has an inner surface 12b' and a sidewall 12b". The sidewall 12b" extends from the inner surface 12b' toward the third sub-body 12a, but does not extend beyond a top surface of the second sensor 42. In the embodiment, the second sensor 42 is disposed in the third chamber 12c, so as to detect the air flowing into the third chamber 12c. In the embodiment, the second sensor 42 is at least one selected from the group consisting of a thermometer, a hygrometer and a combination thereof.

Please refer to FIG. 3 again. The third compartment 1c includes a fifth sub-body 13a, a sixth body 13b and a carrying partition 13c. The fifth sub-body 13a and the sixth body 13b are connected to each other, and the carrying partition 13c is disposed between the fifth sub-body 13a and the sixth sub-body 13b, so that the inner space enclosed by the fifth sub-body 13a and the sixth sub-body 13b is divided to form a fourth chamber 13d disposed between the fifth sub-body 13a and the carrying partition 13c, and to form a fifth chamber 13e disposed between the sixth sub-body 13b and the carrying partition 13c. The inner space enclosed by the fifth sub-body 13a and the sixth sub-body 13b remains an opening in communication with the environment outside the third compartment 1c. Because of the carrying partition 13c, the opening is also divided into a second inlet 13f and a second outlet 13g. The second inlet 13f is disposed between the fifth sub-body 13a and the carrying partition 13c and the second inlet 13f is in fluid communication with the fourth chamber 13d. The second outlet 13g is disposed between the sixth sub-body 13b and the carrying partition 13c, and the second outlet 13g is in fluid communication with the fifth chamber 13e. Both of the second inlet 13f and the second outlet 13g are disposed on the same side of the third compartment 1c. In addition, the carrying partition 13c has a second communication opening 13h. The fourth chamber 13d and the fifth chamber 13e are in fluid communication with each other through the second communication opening 13h.

In the embodiment, the carrying partition 13 has an exposed portion (not designated by a reference sign) extended to an exterior of the third compartment 1c and having a connector 13j. The connector 13j allows the flexible circuit board 5 to be inserted to connect, and provides the carrying partition 13c with electrical connection and signal connection. In addition, the fifth sub-body 13a has a fourth connection through hole 13i. The fourth connection through hole 13i allows the flexible circuit board 5 to be inserted to connect to the second actuator 32. The fourth connection through hole 13i is sealed after connection, to avoid the air flowing into the fourth chamber 13d therethrough. Consequently, the air is introduced into the fourth chamber 13d through the second inlet 13f merely.

In the embodiment, the fine particle detecting base 2 is disposed between the fourth chamber 13d and the carrying partition 13c of the third compartment 1c. The fine particle detecting base 2 has a detecting channel 21 and a receiving slot 22. The receiving slot 22 is disposed in one end of the detecting channel 21 and in fluid communication with the detecting channel 21. The third sensor 43 is carried on the carrying partition 13c and located within the detecting channel 21 of the fine particle detecting base 2. The third sensor 43 detects the air flowing in the detecting channel 21. In the embodiment, the carrying partition 13c can be for example a circuit board, so that the fine particle detecting base 2 and the third sensor 43 are carried on the carrying partition 13c with electrical connection and signal connection.

In the embodiment, the fine particle detecting base 2 further includes a laser 23 and a light-beam channel 24. The laser 23 is electrically connected to the carrying partition 13c. The light-beam channel 24 extends from the laser 23 and connects to the detecting channel 21 perpendicularly. In other words, the light-beam channel 24 and the detecting channel 21 are in communication with each other perpendicularly. Thus, the laser 23 emits a light beam through the light-beam channel 24 to irradiate the detecting channel 21, so that suspended particles in the detecting channel 21 are irradiated to generate scattered light spots. The scattered light spots are projected on the third sensor 43 for the third sensor 43 detecting.

In the embodiment, the third sensor 43 can be for example a light detecting sensor. The light detecting sensor detects the scattered light spots generated by the suspended particles, so as to calculate accordingly the sizes and the concentration of the suspended particles contained in the air. In the embodiment, the light detecting sensor is a PM 2.5 sensor.

Please refer to FIGS. 4 to 6 again. In the embodiment, the actuation-and-detecting module is applied to a thin portable device 10. The thin portable device 10 includes a first though aperture 10a, a second through aperture 10b, a third through aperture 10c and a fourth through aperture 10d. The first though aperture 10a, the second through aperture 10b, the third through aperture 10c and the fourth through aperture 10d are opened on the same sidewall of the thin portable device 10. The actuation-and-detecting module is assembled within the thin portable device 10. The first inlet 11f of the first compartment 1a is spatially corresponding to the first through aperture 10a. The first outlet 11g of the first compartment 1a is spatially corresponding to the second through aperture 10b. The gas through hole 12d of the second compartment 1b is spatially corresponding to the third through aperture 10c. The second inlet 13f and the second outlet 13g of the third compartment 1c are spatially corresponding to the fourth through aperture 10d. In that, the air outside the thin portable device 10 can be introduced into the thin portable device 10 for detecting. First, the air inhaled in the thin portable device 10 flows from the first chamber 11d into the second chamber 11e. By driving the first actuator 31 to actuate the operation of air transportation, a negative pressure is formed in the first chamber 11d, and air is introduced into the first chamber 11d through the first inlet 11f, and then flows into the second chamber 11e through the first communication opening 11h. As the first actuator 31 continuously actuates the operation of air transportation, the air introduced into the second chamber 11e is discharged out from the first outlet 11g, so as to achieve air transportation in one way for detecting. Second, the fourth sub-body 12a and the fifth sub-body 12b isolate the third chamber 12c as an independent space, so that the second sensor 42 disposed within the third chamber 12c can detect the air without interference. Third, the third compartment 1c introduces the air into the third compartment 1c by the second actuator 32 and the concentration of the fine particles is measured by utilizing the third sensor 43. The actuation-and-detecting module of the present disclosure can prevent the plurality of sensors from the influence of various interfering factors (heat generated by the actuator, or some gas pollution, heat and other interfering substance generated by other components of the thin portable device 10). Furthermore, with the arrangement of the plurality of actuators, the air is inhaled in and discharged out. It increase the speed of transporting the air to the surfaces of the plurality of sensors for detecting, thereby improving the detecting efficiency of the plurality of sensors, and achieving the purpose of introducing the "actual air" into the thin portable device 10 by the actuation-and-detecting module. The "actual air" means that the properties of target air in the actuation-and-detecting module are the same as the properties of the ambient air outside the thin portable device 10.

The characteristics of the actuation-and-detecting module is described as the above. The structures and actions of the first actuator 31 and the second actuator 32 are described as the following.

Please refer to FIGS. 7A to 8A. In the embodiment, the first actuator 31 is a gas pump including an air inlet plate 311, a resonance plate 312, a piezoelectric actuator 313, an insulation plate 314 and a conducting plate 315 stacked and assembled sequentially. The air inlet plate 311 has at least one inlet aperture 311a, at least one convergence channel 311b and a convergence chamber 311c. The numbers of the inlet aperture 311a and the convergence channel 311b are the same. In the embodiment, the numbers of the inlet aperture 311a and the convergence channel 311b are exemplified by four for each respectively but not limited thereto. The four inlet aperture 311a penetrate through the four convergence channels 311b respectively, and the four convergence channels 311b converges to the convergence chamber 311c.

In the embodiment, the resonance plate 312 is assembled on the air inlet plate 311 by means of attaching. The resonance plate 312 has a central aperture 312a, a movable part 312b and a fixed part 312c. The central aperture 312a is located in the center of the resonance plate 312 and is aligned with the convergence chamber 311c of the air inlet plate 311. The region of the resonance plate 312 around the central aperture 312a and corresponding to the convergence chamber 311c is the movable part 312b. The region of the periphery of the resonance plate 312 securely attached on the air inlet plate 311 is the fixed part 312c.

In the embodiment, the piezoelectric actuator 313 includes a suspension plate 313a, an outer frame 313b, at least one connection component 313c, a piezoelectric element 313d, at least one vacant space 313e and a bulge 313f. The suspension plate 313a is a square structure and has a first surface 3131a and a second surface 3132a. The first surface 3131a is opposite to the second surface 3132a. The outer frame 313b is arranged around the suspension plate 313a. The outer frame 313b has a coupling surface 3131b and a bottom surface 3132b. The at least one connection component 313c is connected between the suspension plate 313a and the outer frame 313b for elastically supporting the suspension plate 313a. The vacant spaces 313e are formed among the suspension plate 313a, the outer frame 313b and the connection components 313c for the air flowing therethough.

In addition, the suspension plate 313a has the bulge 313f disposed on the first surface 3131a. In the embodiment, the bugle 313f is formed by using an etching process, in which the region between the peripheral edge of the bugle 313f and the junction at the connection components 313c is recessed. Accordingly, the bulge 313f of the suspension plate 313a is higher than the first surface 3131a to form a stepped structure.

Figure 8A:
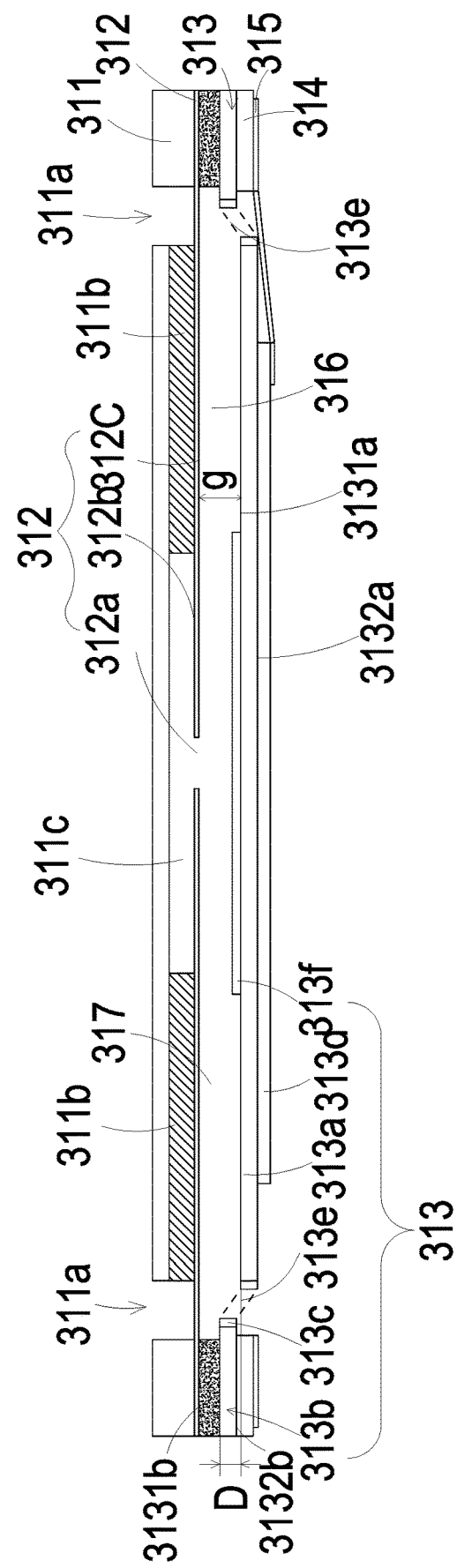
FIG. 8A is a schematic cross-sectional view illustrating the first actuator of the actuation-and-detecting module according to the embodiment of the present disclosure.

Please refer to FIG. 8A again. In the embodiment, the suspension plate 313a may be further processed by using a stamping method, by which the outer frame 313b, the at least one connection component 313c, and the suspension plate 313a have a concave profile in cross section, as shown in FIG. 8A. The stamping method makes the suspension plate 313a away from the resonance plate 312 a distance D, which can be adjusted by the at least one connection component 313c formed between the suspension plate 313a and the outer frame 313b. Consequently, the top surface of the bulge 313f and the first surface 3131a of the suspension plate 313a are not coplanar with the coupling surface 3131b of the outer frame 313b. Namely, the top surface of the bulge 313f and the first surface 3131a are lower than the coupling surface 3131b of the outer frame 313b, and the second surface 3132a of the suspension plate 313a is lower than the bottom surface 3132b of the outer frame 313b. In the embodiment, the piezoelectric element 313d is attached on the second surface 3132a of the suspension plate 313a and aligned with the bulge 313f. In response to an applied voltage, the piezoelectric element 313d is deformed by the piezoelectric effect to drive the suspension plate 313a to undergo the bending vibration. By utilizing a small amount of adhesive and applying the same to the coupling surface 3131b of the outer frame 313b, the piezoelectric actuator 313 is attached to the fixed part 312c of the resonance plate 312 after heat-pressing treatment, thereby assembling the piezoelectric actuator 313 and the resonance plates 312 in combination.

In addition, the insulation plate 314 and the conducting plate 315 are both thin frame-shaped sheets, which are sequentially stacked under the piezoelectric actuator 313. In the embodiment, the insulation plate 314 is attached to the bottom surface 3132b of the outer frame 313b of the piezoelectric actuator 313.

Please refer to FIG. 8A again. After the air inlet plate 311, the resonance plate 312, the piezoelectric actuator 313, the insulation plate 314 and the conducting plate 315 of the first actuator 31 are stacked and assembled sequentially, a chamber gap g is formed between the first surface 3131a of the suspension plate 313a and the resonance plate 312. Since the distance between the suspension plate 313a and the resonance plate 312 will influence the transportation efficiency of the first actuator 31, it is very important to maintain the chamber gap g for providing a stable transportation efficiency of the first actuator 31. The suspension plate 313a of the first actuator 31 is processed by the stamping method as described above, and it makes the suspension plate 313a disposed further away from the resonance plate 312. Consequently, the top surface of the bulge 313f and the first surface 3131a of the suspension plate 313a are not coplanar with the coupling surface 3131b of the outer frame 313b. Namely, the top surface of the bulge 313f and the first surface 3131a of the suspension plate 313a are lower than the coupling surface 3131b of the outer frame 313b, and the second surface 3132a of the suspension plate 313a is lower than the bottom surface 3132b of the outer frame 313b. In this way, the entire structure may be improved by adopting the stamping method to process the suspension plate 313a. The space between the suspension plate 313a of the piezoelectric actuator 313 and the resonance plate 312 is adjustable due to the stamping method, by which the adjustable chamber gap g is realized. That is, the design of a chamber space 316 is improved by processing the suspension plate 313a of the piezoelectric actuator 23 to be disposed further away from the resonance plate 312. The desired chamber gap g may be satisfied by simply adjusting the distance D, as described above. It simplifies the structural design regarding the adjustment of the chamber gap g, and it also achieves the advantages of simplifying the process and shortening the processing time.

Figure 8B:
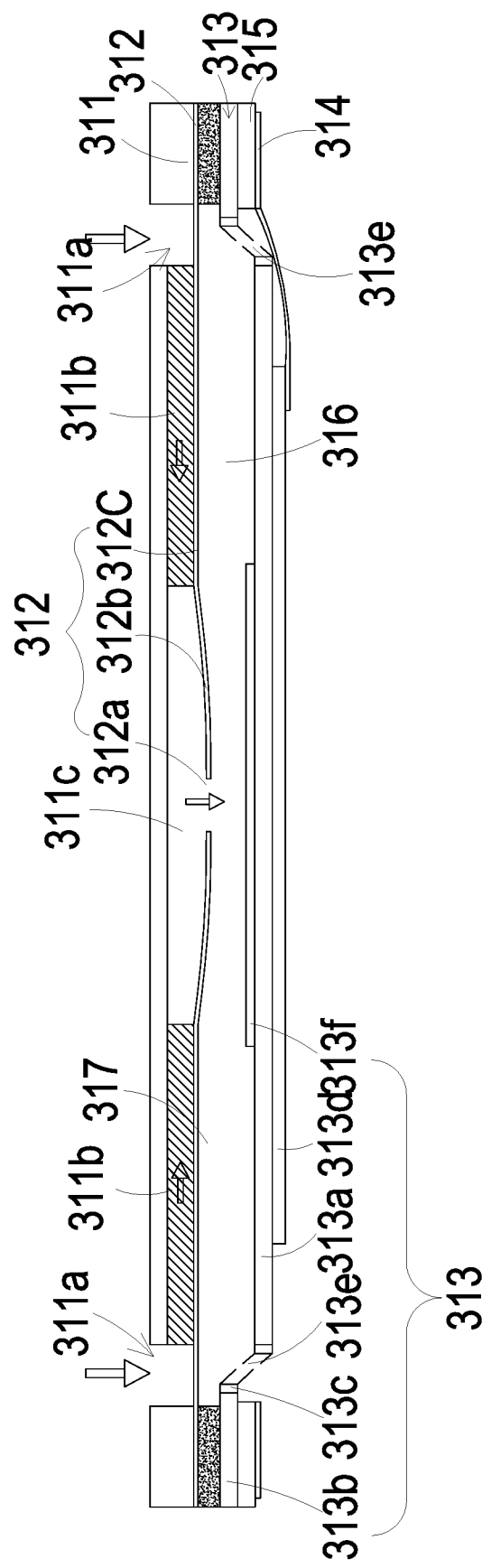
FIG. 8B through FIG. 8D are schematic views illustrating actions of the first actuator of the actuation-and-detecting module of the present disclosure.
Figure 8C:
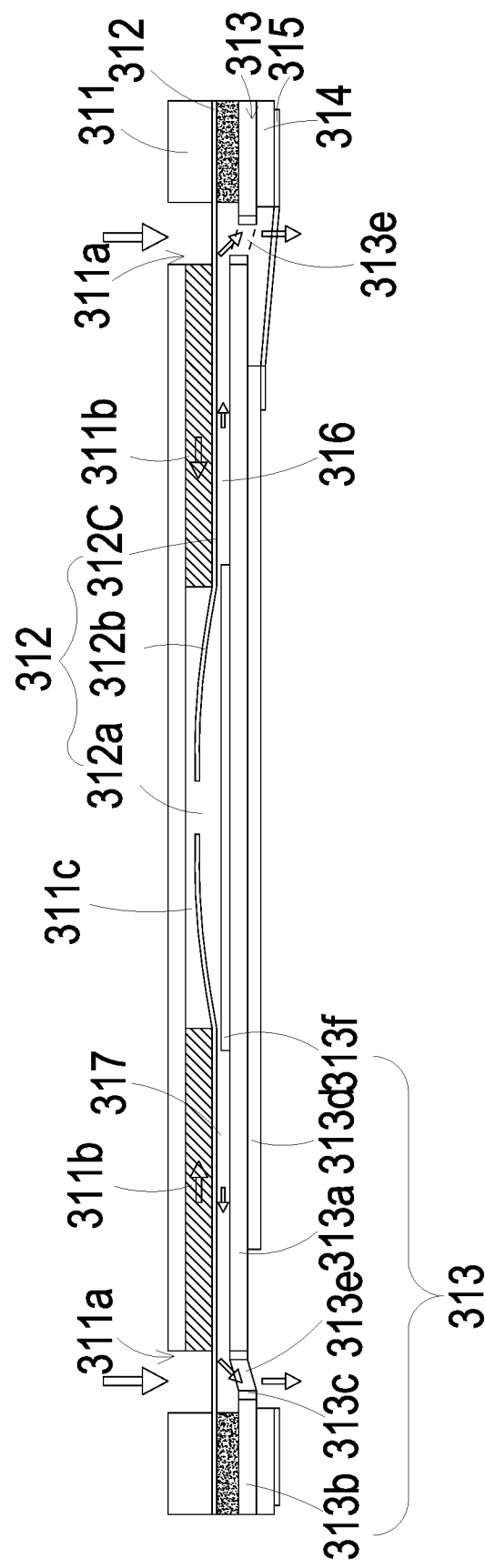
Figure 8D:
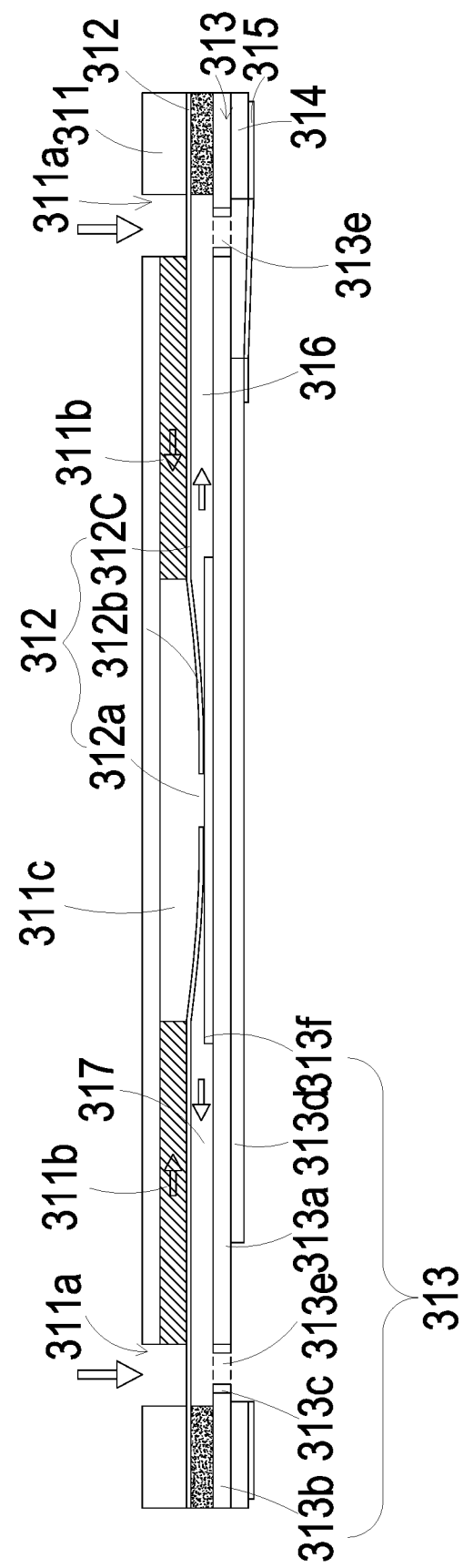

FIGS. 8B through 8D are schematic views illustrating actions of the first actuator of the actuation-and-detecting module of the present disclosure. Please refer to FIG. 8B firstly. When the piezoelectric element 313d of the piezoelectric actuator 313 is deformed in response to an applied voltage, the suspension plate 313a is driven to displace in the direction away from the air inlet plate 311. In that, the volume of the chamber space 316 is increased, a negative pressure is formed in the chamber space 316, and the air in the convergence chamber 311c is inhaled into the chamber space 316. At the same time, the resonance plate 312 is in resonance and thus displaced synchronously in the direction away from the air inlet plate 311. Thereby, the volume of the convergence chamber 311c is increased. Since the air in the convergence chamber 311c flows into the chamber space 316, the convergence chamber 311c is also in a negative pressure state, and the air is inhaled into the convergence chamber 311c along the inlet aperture 311a and the convergence channel 311b. Please refer to FIG. 8C, the piezoelectric element 313d drives the suspension plate 313a to be displaced toward the air inlet plate 311 to compress the chamber space 316. Thus, the air contained in the chamber space 316 is transported to flow through the vacant spaces 313e in the direction away from the air inlet plate 311 and it achieves the effect of air transportation. Similarly, the resonance plate 312 is actuated in resonance by the suspension plate 313a and displaced toward the air inlet plate 311. Thus, the air contained in convergence chamber 311c is compressed synchronously and pushed to the chamber space 316. Finally, as shown in FIG. 8D. As the suspension plate 313a is driven to displace in the direction away from the air inlet plate 311 and the resonance plate 312 is also driven to displace in the direction away from the air inlet plate 311 at the same time. In that, the resonance plate 312 pushes the air in the chamber space 316 toward the vacant space 313e, and the volume of the convergence chamber 311c is increased. Thus, the air can continuously flow through the inlet aperture 311a and the convergence channel 311b and be converged in the confluence chamber 311c. By repeating the actions shown in the above continuously, the first actuator 31 can continuously inhale the air through the inlet aperture 311a and transport the air out through the vacant spaces 313e in the direction away from the air inlet plate 311. It achieves the effect of transporting the air to the first sensor 41. The first sensor 41 is provided with the air for measurement, thereby improving the sensing efficiency.

Please refer to FIG. 8A again. In another embodiment, the first actuator 31 can be a micro-electromechanical-systems gas pump formed by a micro-electromechanical-systems method. The air inlet plate 311, the resonance plate 312, the piezoelectric actuator 313, the insulation plate 314, and the conducting plate 315 can all be made through a surface micromachining technique to reduce the volume of the first actuator 31.

Figure 9:
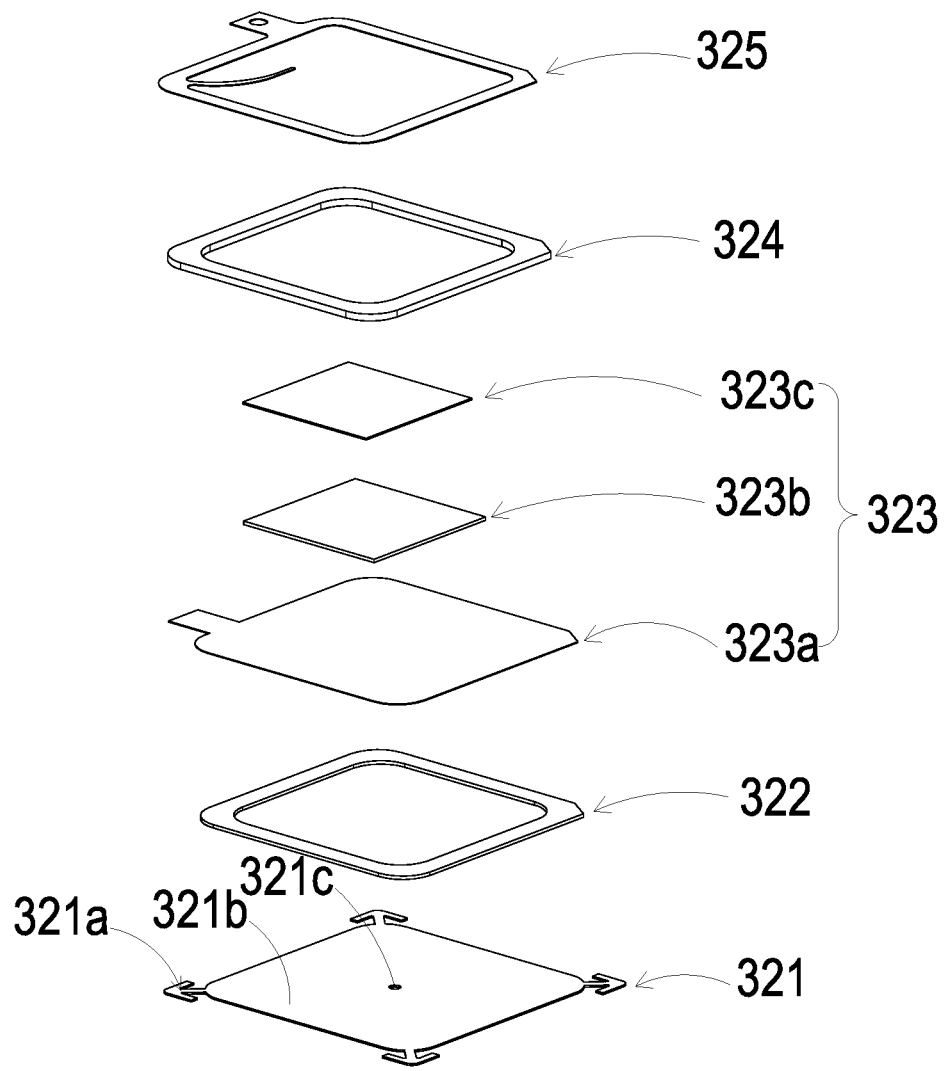
FIG. 9 is an exploded view illustrating a second actuator of the actuation-and-detecting module according to an embodiment of the present disclosure.

Please refer to FIG. 9. In the embodiment, the second actuator 32 includes a nozzle plate 321, a chamber frame 322, an actuation element 323, an insulation frame 324 and a conducting frame 325 stacked on each other sequentially. The nozzle plate 321 includes a plurality of brackets 321a, a suspension plate 321b and a central aperture 321c. The suspension plate 321b is permitted to undergo a bending vibration. The plurality of brackets 321a are connected to the edge of the suspension plate 321b. In the embodiment, there are four brackets 321a, which are connected to four corners of the suspension plate 321b, respectively, but the present disclosure is not limited thereto. The central aperture 321c is formed at the center of the suspension plate 321b.

The chamber frame 322 is carried and stacked on the suspension plate 321b. The actuation element 323 is carried and stacked on the chamber frame 322 and includes a piezoelectric carrying plate 323a, an adjusting resonance plate 323b and a piezoelectric plate 323c. The piezoelectric carrying plate 323a is carried and stacked on the chamber frame 322. The adjusting resonance plate 323b is carried and stacked on the piezoelectric carrying plate 323a. The piezoelectric plate 323c is carried and stacked on the adjusting resonance plate 323b. As the piezoelectric plate 323c is actuated by an applied voltage, the piezoelectric plate 323c deforms to drive the piezoelectric carrying plate 323a and the adjusting resonance plate 323b to bend and vibrate in the reciprocating manner The insulation frame 324 is carried and stacked on the piezoelectric carrying plate 323a of the actuation element 323. The conducting frame 325 is carried and stacked on the insulation frame 324. A resonance chamber 326 is defined by the actuation element 323, the chamber frame 322 and the suspension plate 321b collaboratively. The adjusting resonance plate 323b is thicker than the piezoelectric carrying plate 323a.

Figure 10A:
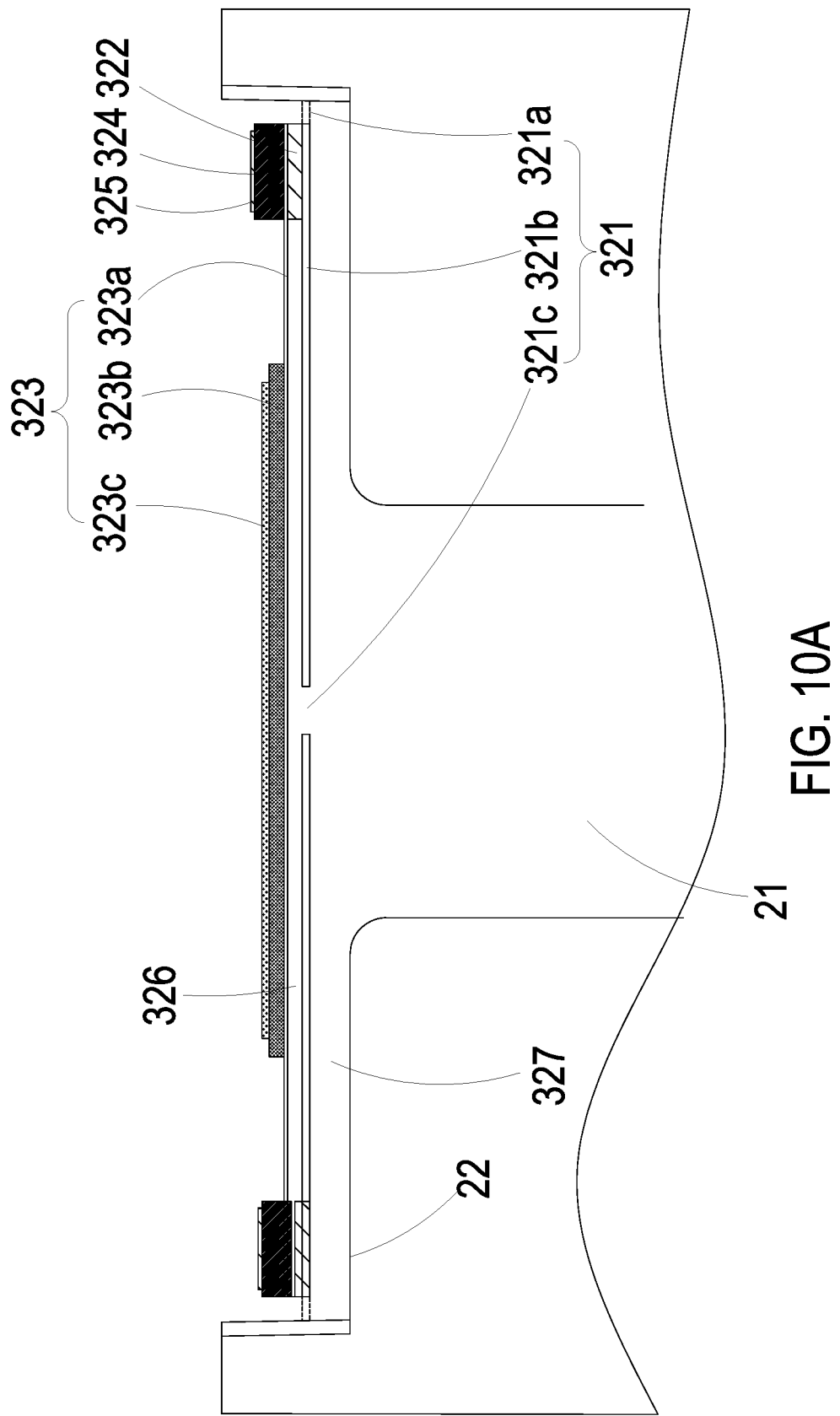
FIG. 10A is schematic cross-sectional view illustrating the second actuator disposed on the fine particle detecting base of the actuation-and-detecting module according to an embodiment of the present disclosure.
Figure 10B:
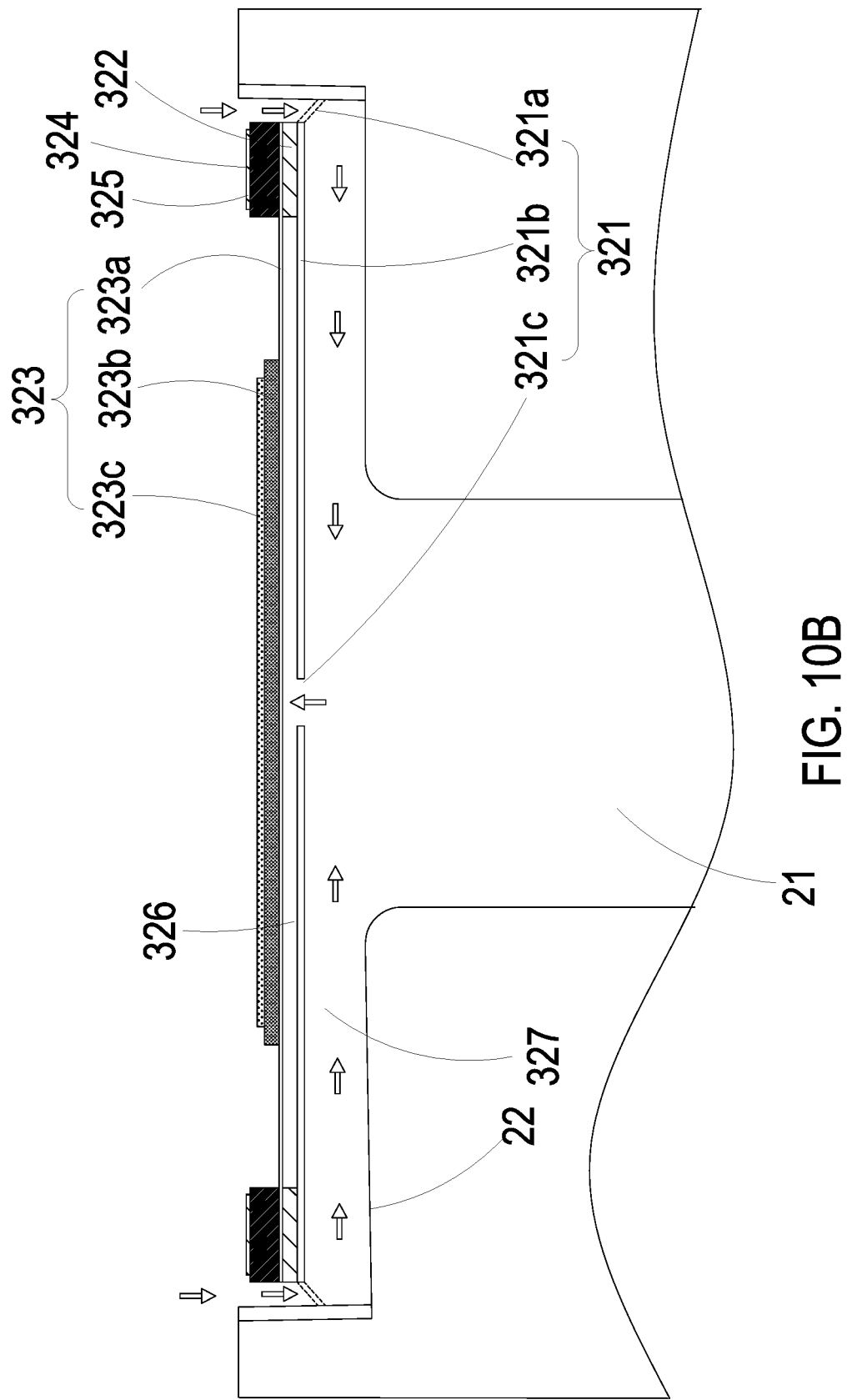
FIG. 10B and FIG. 10C are schematic views illustrating actions of the second actuator disposed on the fine particle detecting base of the actuation-and-detecting module of the present disclosure.
Figure 10C:
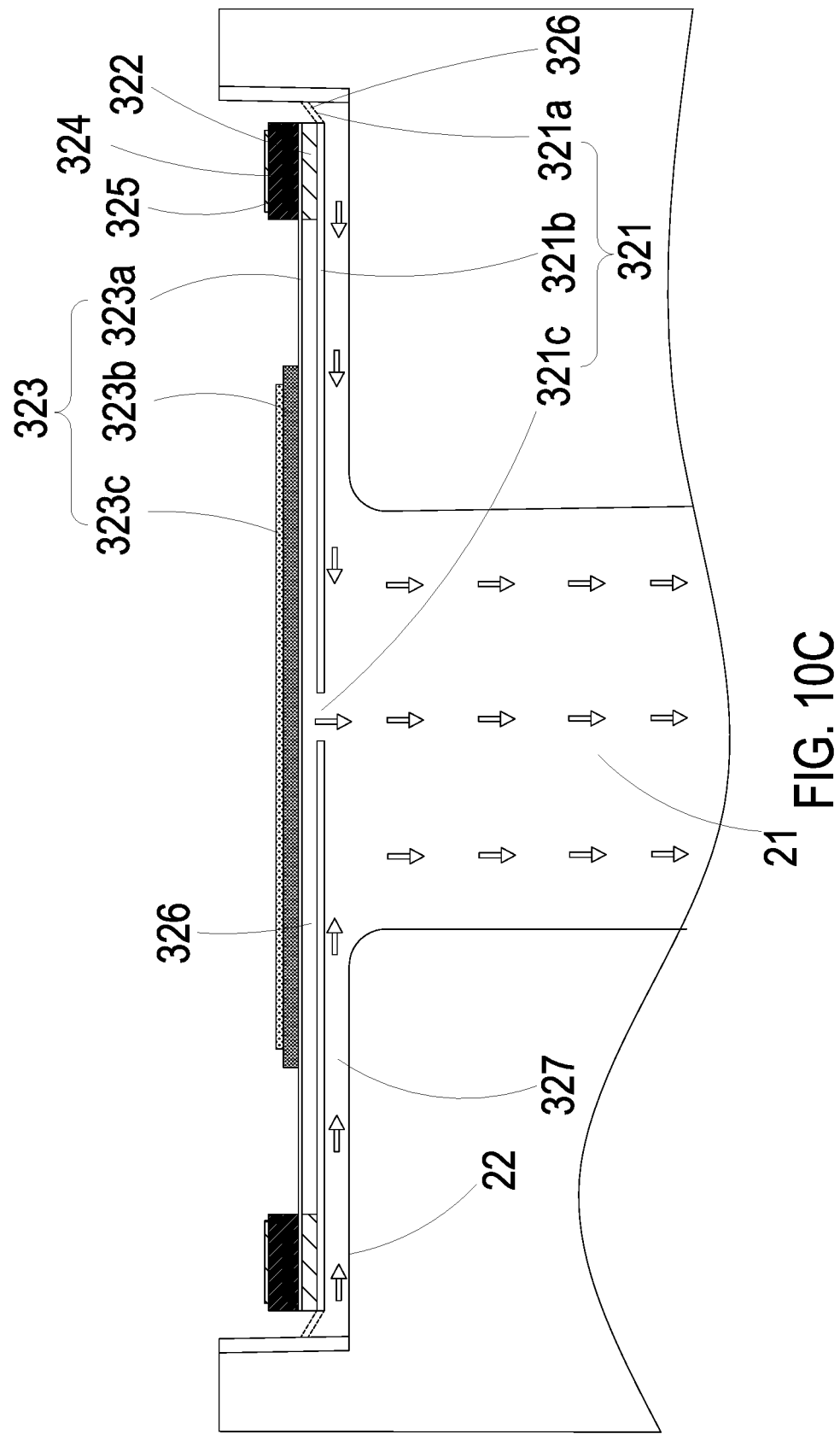

Please refer to FIGS. 10A to 10B. FIGS. 10B and FIG. 10C are schematic views illustrating actions of the second actuator disposed on the fine particle detecting base of the actuation-and-detecting module of the present disclosure. As shown in FIG. 10A, the second actuator 32 is disposed on the receiving slot 22 of the fine particle detecting base 2 through the plurality of bracket 321a. The nozzle plate 321 is spaced apart from the bottom surface of the receiving slot 22. An airflow chamber 327 is formed between the nozzle plate 321 and the receiving slot 22. As shown in FIG. 10B, when the piezoelectric plate 323c of the actuation element 323 is actuated by an applied voltage, the piezoelectric plate 323c of the actuation element 323 is deformed by the piezoelectric effect, and the adjusting resonance plate 323b and the piezoelectric carrying plate 323a are driven to vibrate synchronously. Thereby, the nozzle plate 321 is driven to move due to the Helmholtz resonance effect and the actuation element 323 is displaced in a direction away from the bottom of the receiving slot 22. Since the actuation element 323 is displaced in the direction away from the bottom of the receiving slot 22, the volume of the airflow chamber 327 formed between the nozzle plate 321 and the bottom of the receiving slot 22 is expended, and a negative pressure is formed in the airflow chamber 327. The air outside the second actuator 32 is transported into the airflow chamber 327 through the vacant spaces formed among the plurality of brackets 321a of the nozzle plate 321 and the lateral walls of the receiving slot 22 due to the pressure gradient, and is further compressed. As shown in FIG. 10C, the air flows into the airflow chamber 327 continuously and a positive pressure is formed in the airflow chamber 327. At the meantime, the actuation element 323 is driven to vibrate in a direction toward the bottom of the receiving slot 22 in response to the applied voltage, the volume of the airflow chamber 327 is shrunken and the air contained in the airflow chamber 327 is pushed to flow into the detecting channel 21. Consequently, the actuation element 323 provides the third sensor 43 with the air, so as to measure the concentration of the suspended particles contained in the air through the third sensor 43.

Figure 11:
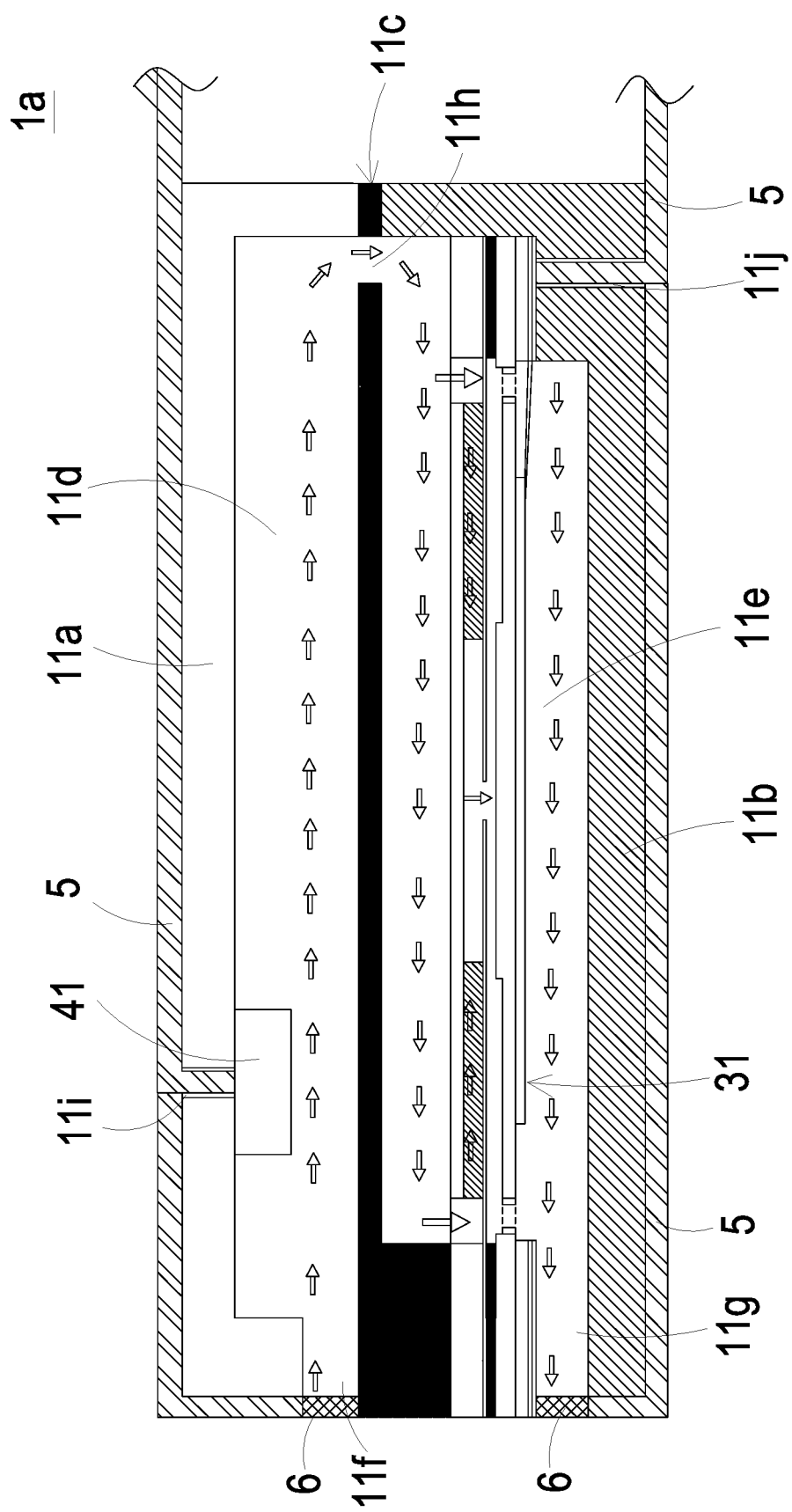
FIG. 11 is a schematic cross-sectional view illustrating a first compartment of an actuation-and-detecting module according to another embodiment of the present disclosure.

Please refer to FIG. 11. In another embodiment, the first compartment 1a of the actuation-and-detecting module further includes at least one valve 6. In the embodiment, there are two valves 6 disposed on the first inlet 11f and the first outlet 11g, respectively. The first inlet 11f and the first outlet 11g can be opened and closed by utilizing the valves 6, respectively. The valves 6 seal the first inlet 11f and the first outlet 11g. As the valves 6 are in the closed state, the inner space enclosed by the first compartment 1a is completely isolated from the environment outside the first compartment 1a, and vise versa. For example, since volatile organic compounds have low boiling points and are easily influenced by external environmental factors, the first inlet 11f and the first outlet 11g are closed by the valves 6 during the operation of measuring the volatile organic compounds. The influence of the external factors on the inside of the first compartment 1a is isolated by the first sub-body 11a and the second sub-body 11b. In addition, the first partition 11c blocks the first actuator 31 from interfering with the first sensor 41. Thus, the first sensor 41 can sense the content of volatile organic compounds in the air inside the first compartment 1a without being affected by environmental factors.

Figure 12A:
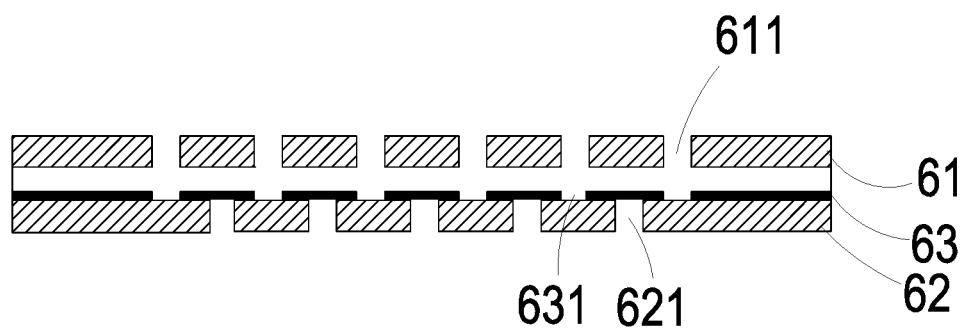
FIG. 12A is a schematic cross-sectional view illustrating a valve of the actuation-and-detecting module according to another embodiment of the present disclosure.
Figure 12B:
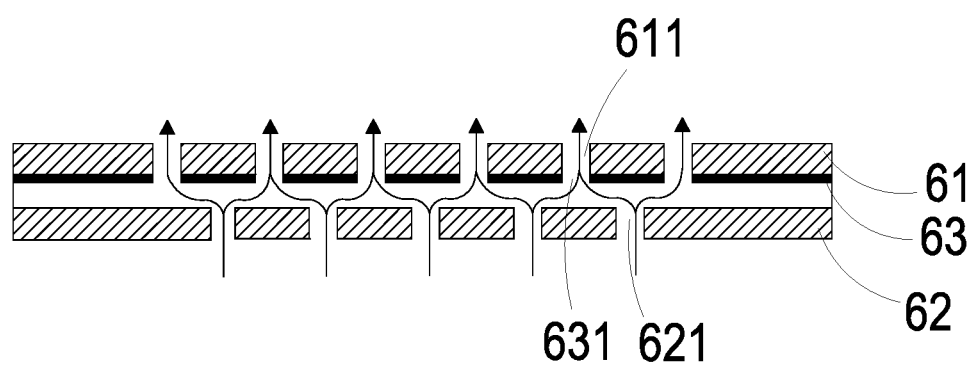
FIG. 12B is a schematic cross-sectional view illustrating action of valve of the actuation-and-detecting module according to another embodiment of the present disclosure.

Please refer to FIGS. 12A and 12B. In the embodiment, the valve 6 includes a stationary component 61, a sealing component 62 and a displacement component 63. The displacement component 63 is disposed between the stationary component 61 and the sealing component 62. The stationary component 61 has a plurality of first orifices 611. The displacement component 63 has a plurality of second orifices 631 respectively corresponding in position to the plurality of first orifices 611 of the stationary component 61. That is, the plurality of first orifices 611 of the stationary component 61 are aligned with the plurality of second orifices 631 of the displacement component 63. The sealing component 62 has a plurality of third orifices 621. The plurality of third orifices 621 of the sealing component 62 are misaligned with the plurality of first orifices 611 of the stationary component 61. The stationary component 61, the sealing component 62 and the displacement component 63 of the valve 6 are controlled by connecting to a processor (not shown) through the flexible circuit board 5, so as to control the displacement component 63 to move toward the stationary component 61 and make the valve 6 in an open state, as shown in FIG. 12B.

In a first aspect of the valve 6 in the present disclosure, the displacement component 63 is made of a charged material, and the stationary component 61 is made of a bipolar conductive material. The stationary component 61 is electrically connected to the processor on the flexible circuit board 5, so as to control the polarity (positive electrical polarity or negative electrical polarity) of the stationary component 61. In case that the displacement component 63 is made of a negative-charged material, and the valve 6 needs to be controlled to open, the stationary component 61 is controlled to form a positive electrode. In that, the displacement component 63 and the stationary component 61 are maintained in the opposite polarity, so that the displacement component 63 moves toward and attaches to the stationary component 61, and the valve 6 is in an open state (as shown in FIG. 12B). Alternatively, in case that the displacement component 63 is made of a negative-charged material, and the valve 6 needs to be controlled to close, the stationary component 61 is controlled to form a negative electrode. In that, the displacement component 63 and the stationary component 61 are maintained in the same polarity, so that displacement component 63 moves toward and attaches to the sealing component 62, and the valve 6 is in a closed state (as shown in FIG. 12A).

In a second aspect of the valve 6 in the present disclosure, the displacement component 63 is made of a magnetic material, and the stationary component 61 is made of an electromagnet material and can be controlled to change its magnetic polarity. The stationary component 61 is electrically connected to the processer on the flexible circuit board 5, so as to control the polarity (positive magnetic polarity or negative magnetic polarity) of the stationary component 61. In case that the displacement component 63 is made of a negative-magnetic material, and the valve 6 needs to be controlled to open, the stationary component 61 is controlled to form a positive-magnetic pole. In that, the displacement component 63 and the stationary component 61 are maintained in the opposite polarity, so that the displacement component 63 moves toward and attaches to the stationary component 61, and the valve 6 is in the open state (as shown in FIG. 12B). Alternatively, in case that the displacement component 63 is made of a negative-magnetic material, and the valve 6 needs to be controlled to close, the stationary component 61 is controlled to form a negative-magnetic pole. In that, the displacement component 63 and the stationary component 61 are maintained in the same polarity, so that the displacement component 63 moves toward and attaches to the sealing component 62, and the valve 6 is in the closed state (as shown in FIG. 12A).

Figure 3:
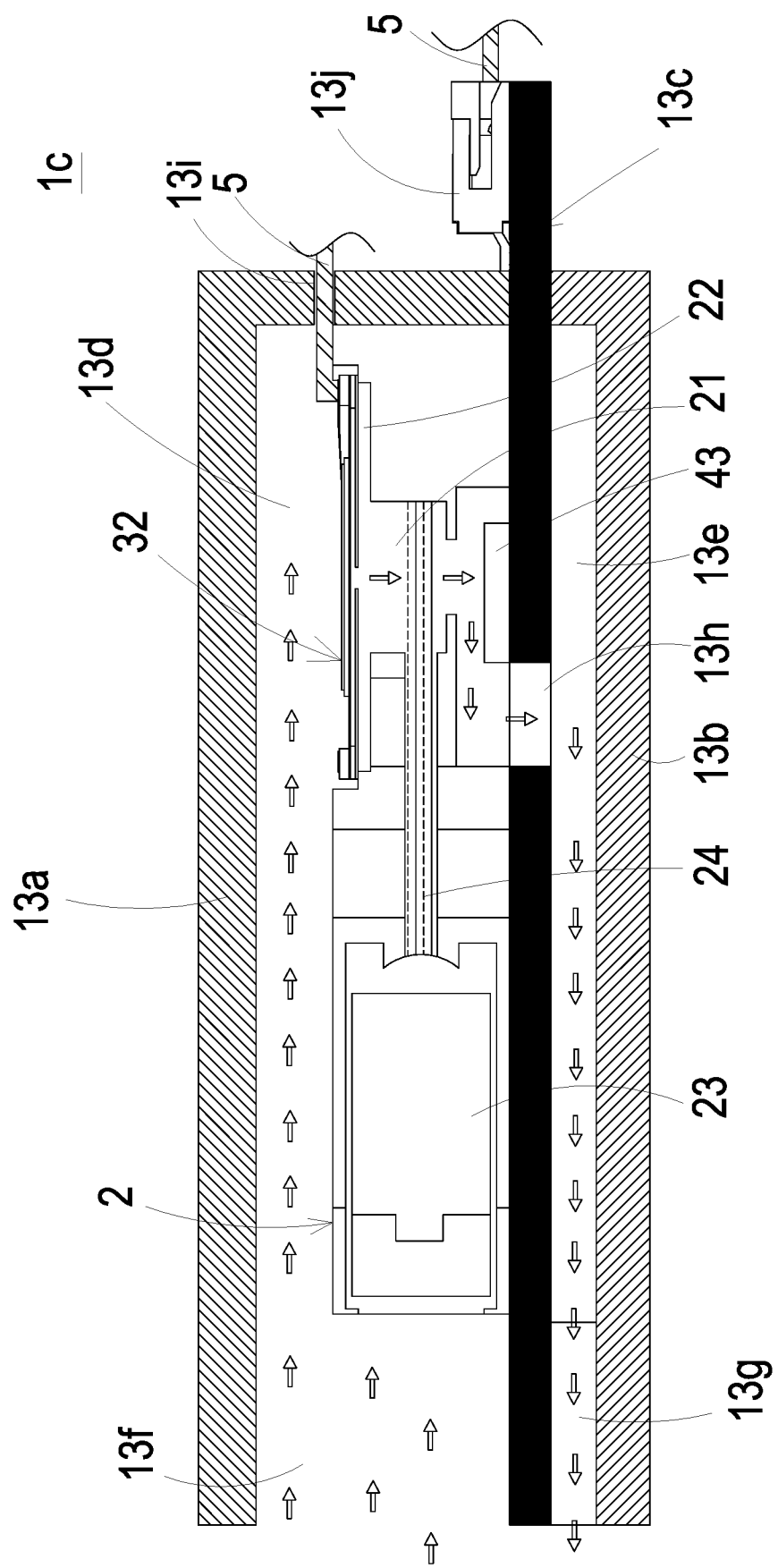
FIG. 3 is a schematic cross-sectional view illustrating a third compartment of the actuation-and-detecting module according to an embodiment of the present disclosure.
Figure 13:
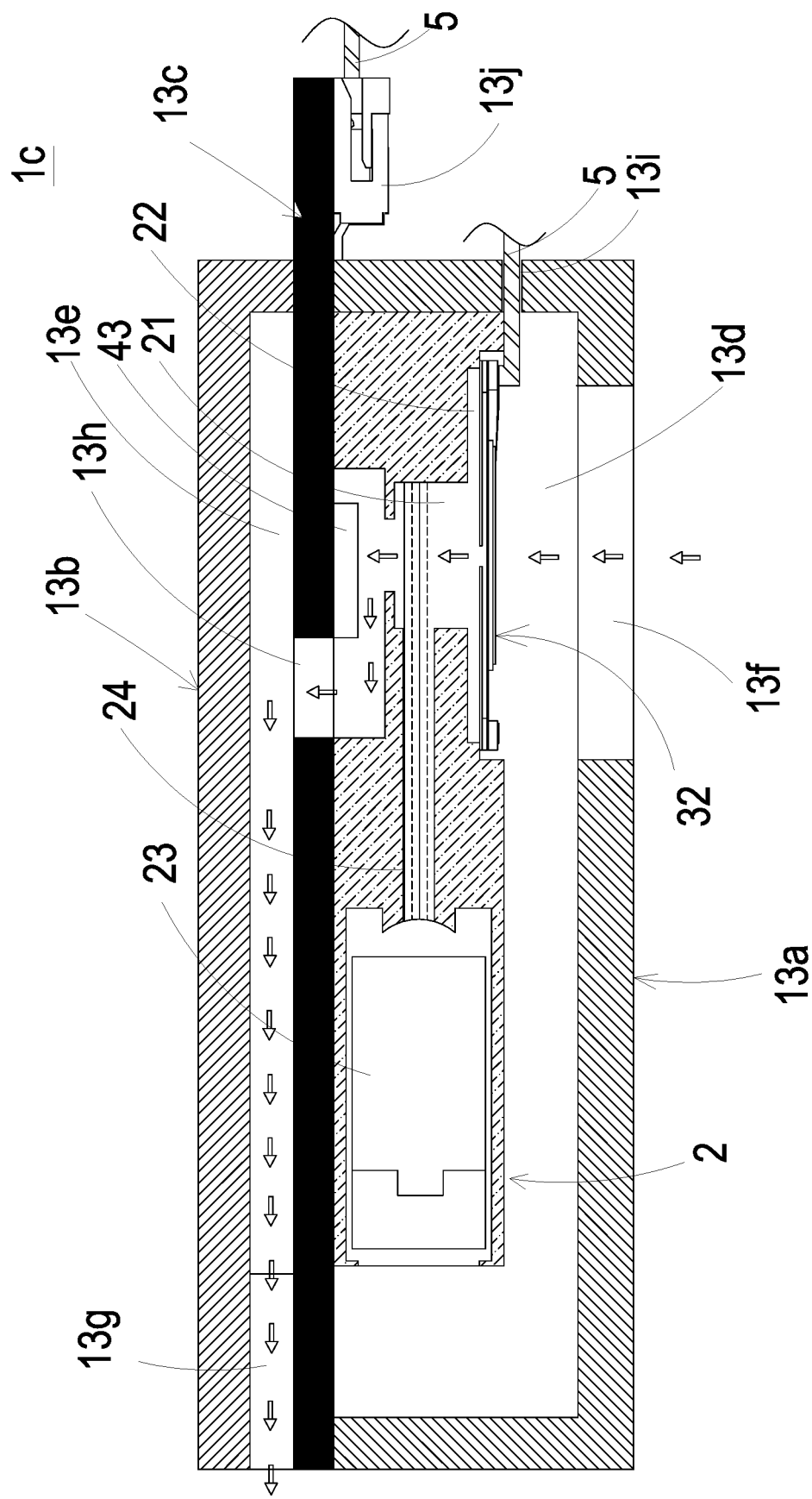
FIG. 13 is a schematic cross-sectional view illustrating a third compartment of the actuation-and-detecting module according to another embodiment of the present disclosure.

Please refer to FIG. 13, which shows a third compartment 1c of the actuation-and-detecting module according to another embodiment. In the embodiment, the second inlet 13f is aligned with the detecting channel 21. That is, the second inlet 13f is disposed directly under the detecting channel 21. Before reaching the detecting channel 21, the air may flow along an airflow path (indicated by the arrows) perpendicular to the detecting channel 21, as shown in FIG. 3. However, in the embodiment illustrated in FIG. 13, it efficiently reduces the airflow path perpendicular to the detecting channel 21, or, more accurately speaking, the position of the second inlet 13f disposed directly under the detecting channel 21 makes the airflow path connect to the detecting channel 21 in a straight direction. In that, the airflow resistance on the airflow path is eliminated as much as possible. When the second actuator 32 is actuated, the air is inhaled from the second inlet 13f and flows along the straight direction into the detecting channel 21 without hindrance, so as to improve the efficiency of air transportation.

Figure 14:
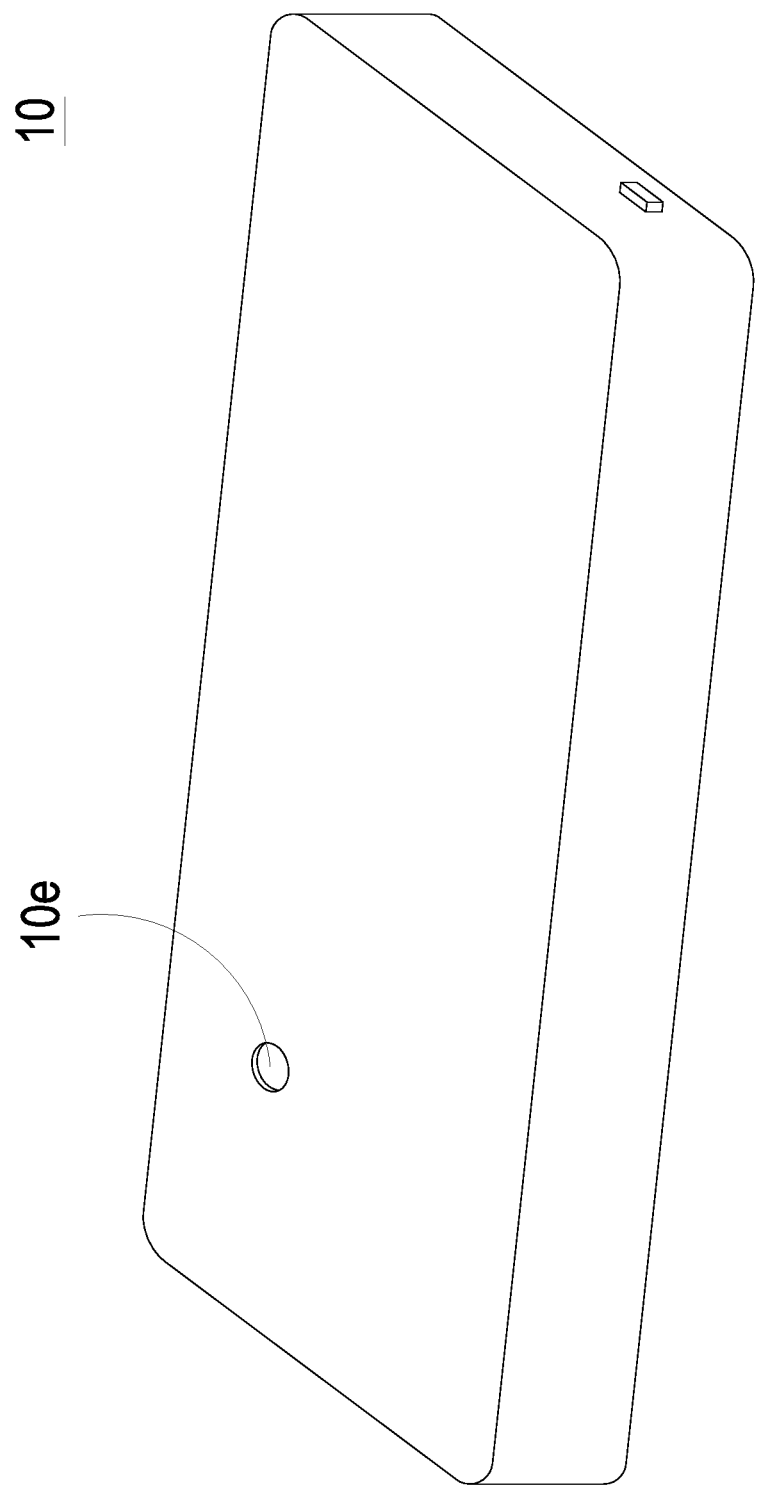
FIG. 14 is a schematic view illustrating a fourth through aperture aligned with the third compartment of the actuation-and-detecting module applied to a thin portable device according to another embodiment of the present disclosure.
Figure 15:
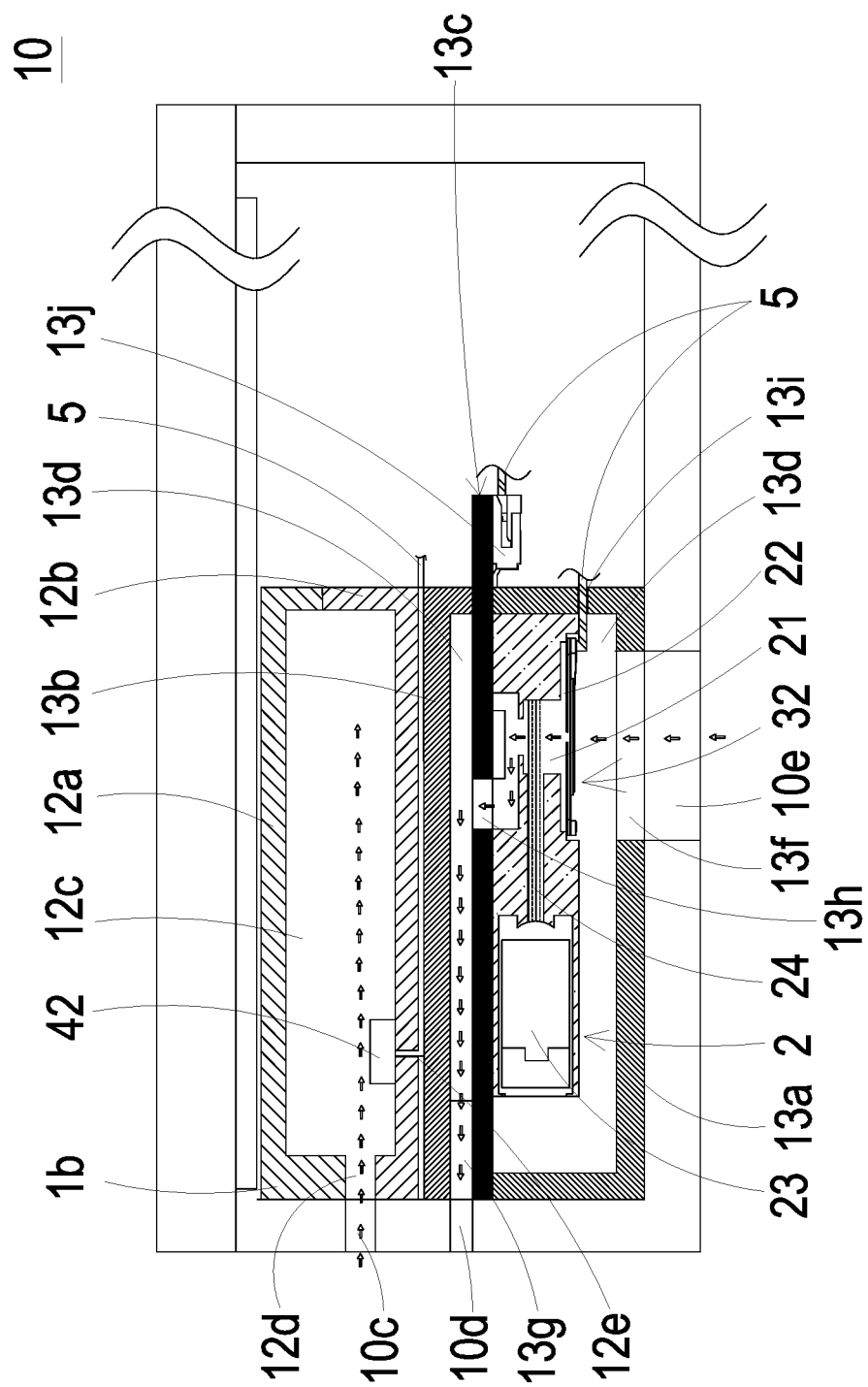
FIG. 15 is a schematic cross-sectional view illustrating the third compartment of the actuation-and-detecting module applied to a thin portable device according to another embodiment of the present disclosure.

Please refer to FIGS. 14 and 15. In case that the actuation-and-detecting module with the third compartment 1c described above is assembled with the thin portable device 10, the thin portable device 10 further includes a fifth through hole 10e. In the embodiment, the fourth through hole 10d of the thin portable device 10 is aligned directly to the second outlet 13g of the third compartment 1c and the fifth through hole 10e is aligned directly to the second inlet 13f of the third compartment 1c, to allow the air to directly flow in and flow out the third compartment 1c, thereby enhancing the efficiency of air transportation.

In summary, the present disclosure provides an actuation-and-detecting module. By utilizing the recessed suspension plate, the actuator can transport air into the actuation-and-detecting module rapidly and stably, to improve the detecting efficiency. Moreover, with the plurality of compartments to space apart the sensors, when the plurality of sensors are used to sense simultaneously, it benefits to avoid mutual interference and also block the influences of other actuators. As the air outside the thin portable device is introduced into the thin portable device by the actuation-and-detecting module for measurement, the processor and other components of the thin portable device do not influence the sensing operation. Thus, the actuation-and-detecting module can be actually introduced into the thin portable device to achieve the purpose of monitoring the air quality at anytime and anywhere.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An actuation-and-detecting module comprising:
  a main body comprising a plurality of compartments, wherein the plurality of compartments comprises:
    a first compartment having a first chamber, a second chamber, a first partition, a first inlet and a first outlet, wherein space inside the first compartment is divided into the first chamber and the second chamber by the first partition, the first inlet is in fluid communication with the first chamber, the first outlet is in fluid communication with the second chamber, and the first partition has a first communication opening in fluid communication with the first chamber and the second chamber;
    a second compartment integrally combined with the first compartment, and having a third chamber and a gas through hole, wherein space inside the second compartment is defined as the third chamber, and the gas through hole is in fluid communication with the third chamber; and
    a third compartment integrally combined with the first compartment and the second compartment, and having a fourth chamber, a fifth chamber, a carrying partition, a second inlet and a second outlet, wherein space inside the third compartment is divided into the fourth chamber and the fifth chamber by the carrying partition, the second inlet is in fluid communication with the fourth chamber, the second outlet is in fluid communication with the fifth chamber, and the carrying partition has a second communication opening in fluid communication with the fourth chamber and the fifth chamber;
  a fine particle detecting base disposed between the fourth chamber and the carrying partition of the third compartment, and having a detecting channel and a receiving slot, wherein the receiving slot is disposed in one end of the detecting channel and in fluid communication with the detecting channel;
  a plurality of actuators comprising:
    a first actuator disposed between the first partition and the first compartment in the second chamber to allow air to flow into the first chamber through the first inlet, be transported to the second chamber through the first communication opening and be discharged out through the first outlet, so as to achieve air transportation of the first compartment in one way; and
    a second actuator disposed within the receiving slot of the fine particle detecting base and sealing one end of the detecting channel to allow air to flow into the fourth chamber through the second inlet, be transported to the fifth chamber through the second communication opening, and be discharged out through the second outlet, so as to achieve air transportation of the third compartment in one way; and
  a plurality of sensors comprising:
    a first sensor disposed within the first chamber and spaced apart from the first actuator to detect the air flowing through a surface thereof;
    a second sensor disposed within the third chamber to detect the air flowing into the third chamber; and
    a third sensor carried on the carrying partition and located within the detecting channel of the fine particle detecting base to detect the air flowing into the detecting channel.

2. The actuation-and-detecting module according to claim 1, wherein the first compartment comprises a first sub-body and a second sub-body, wherein the first sub-body and the second sub-body are connected to each other, and the first partition is disposed between the first sub-body and the second sub-body, so as to form the first chamber between the first sub-body and the first partition and form the second chamber between the second sub-body and the first partition, wherein the first inlet is disposed between the first sub-body and the first partition and in fluid communication with the first chamber, and the first outlet is disposed between the second sub-body and the first partition and in fluid communication with the second chamber.

3. The actuation-and-detecting module according to claim 1, wherein the second compartment comprises a third sub-body and a fourth sub-body, wherein the third sub-body and the fourth sub-body are connected to each other to define the third chamber.

4. The actuation-and-detecting module according to claim 1, wherein the third compartment comprises a fifth sub-body and a sixth sub-body, wherein the fifth sub-body and the sixth sub-body are connected to each other, and the carrying partition is disposed between the fifth sub-body and the sixth sub-body, so as to form the fourth chamber between the fifth sub-body and the carrying partition and form the fifth chamber between the sixth sub-body and the carrying partition, wherein the second inlet is disposed between the fifth sub-body and the carrying partition and in fluid communication with the fourth chamber, and the second outlet is disposed between the sixth sub-body and the carrying partition and in fluid communication with the fifth chamber.

5. The actuation-and-detecting module according to claim 1, wherein the first sensor is a gas sensor.

6. The actuation-and-detecting module according to claim 5, wherein the gas sensor is at least one selected from the group consisting of an oxygen sensor, a carbon monoxide sensor, a carbon dioxide sensor, a volatile organic compound sensor, a bacterium sensor, a virus sensor, a microorganism sensor and combinations thereof.

7. The actuation-and-detecting module according to claim 1, wherein the second sensor is at least one selected from the group consisting of a thermometer, a hygrometer and a combination thereof, and the third sensor is a light detecting sensor.

8. The actuation-and-detecting module according to claim 7, wherein the light detecting sensor is a PM 2.5 sensor.

9. The actuation-and-detecting module according to claim 1, wherein the first actuator is a micro-electromechanical-systems gas pump.

10. The actuation-and-detecting module according to claim 1, wherein the first actuator is a gas pump comprising:
  an air inlet plate having at least one inlet aperture, at least one convergence channel and a convergence chamber, wherein the at least one inlet aperture allows the air to flow in, and the at least one convergence channel is aligned with the at least one inlet aperture and guides the air from the inlet aperture toward the convergence chamber;

a resonance plate having a central aperture and a movable part, wherein the central aperture is aligned with the convergence chamber and the movable part surrounds the central aperture;

a piezoelectric actuator aligned with the resonance plate;

a conducting plate; and an insulation plate;

wherein the air inlet plate, the resonance plate, the piezoelectric actuator, the insulation plate and the conducting plate are stacked and assembled sequentially, wherein a chamber space is formed between the resonance plate and the piezoelectric actuator, so that the air from the at least one inlet aperture of the air inlet plate is converged to the convergence chamber along the at least one convergence channel and flows into the chamber space through the central aperture of the resonance plate when the piezoelectric actuator is driven, whereby the air is further transported through a resonance between the piezoelectric actuator and the movable part of the resonance plate.

11. The actuation-and-detecting module according to claim 10, wherein the piezoelectric actuator comprises:

a suspension plate being a square structure and having a first surface, a second surface and a bulge, wherein the bulge is disposed on the first surface;

an outer frame arranged around the suspension plate and having a coupling surface;

at least one connection component connected between the suspension plate and the outer frame for elastically supporting the suspension plate; and a piezoelectric element attached on the second surface of the suspension plate to drive the suspension plate to undergo the bending vibration in response to an applied voltage;

wherein the at least one connection component is formed between the suspension plate and the outer frame, the first surface of the suspension plate and the coupling surface of the outer frame are non-coplanar, and a chamber gap is maintained between the first surface of the suspension plate and the resonance plate.

12. The actuation-and-detecting module according to claim 1, wherein the carrying partition is a circuit board, and the fine particle detecting base and the third sensor are carried on the carrying partition with electrical connection and signal connection, wherein the fine particle detecting base comprises a laser electrically connected to the carrying partition, and a light-beam channel extending perpendicularly to and being in communication with the detecting channel to allow a light beam of the laser to irradiate the detecting channel, so that suspended particles in the detecting channel are irradiated to generate scattered light spots projected on the third sensor for detecting, wherein the carrying partition has an exposed portion extended to an exterior of the third compartment and having a connector to allow a flexible circuit board to be inserted to connect and provide the carrying partition with electrical connection and signal connection.

13. The actuation-and-detecting module according to claim 2, wherein the first sub-body has a first connection through hole to allow a flexible circuit board to be inserted to connect to the first sensor, wherein the first connection through hole is sealed after connection so that the air is introduced into the first chamber through the first inlet merely, wherein the second sub-body has a second connection through hole to allow another flexible circuit board to be inserted to connect to the first actuator, wherein the second connection through hole is sealed after connection.

14. The actuation-and-detecting module according to claim 3, wherein the fourth sub-body has a third connection through hole to allow a flexible circuit board to be inserted to connect to the second sensor, wherein the third connection through hole is sealed after connection.

15. The actuation-and-detecting module according to claim 4, wherein the fifth sub-body has a fourth connection through hole to allow a flexible circuit board to be inserted to connect to the second actuator, wherein the fourth connection through hole is sealed after connection.

16. The actuation-and-detecting module according to claim 1, wherein the second inlet is aligned with the detecting channel to form direct convection of the air.

17. The actuation-and-detecting module according to claim 1, wherein the second actuator comprises:

a nozzle plate having a plurality of brackets, a suspension plate and a central aperture, wherein the suspension plate is permitted to undergo a bending vibration, the plurality of brackets are adjacent to and connected to edges of the suspension plate, the central aperture is aligned with the center of the suspension plate, the suspension plate is disposed on the receiving slot of the fine particle detecting base through the plurality of brackets for elastically supporting the suspension plate, an airflow chamber is defined between the nozzle plate and the receiving slot, and at least one vacant space is defined among the plurality of brackets and the suspension plate;

a chamber frame carried and stacked on the suspension plate;

an actuation element carried and stacked on the chamber frame, wherein the actuation element is configured to bend and vibrate in a reciprocating manner by an applied voltage;

an insulation frame carried and stacked on the actuation element; and a conducting frame carried and stacked on the insulation frame;

wherein a resonance chamber is defined by the actuation element, the chamber frame and the suspension plate collaboratively, wherein by driving the actuation element to drive the nozzle plate to generate a resonance, the suspension plate of the nozzle plate vibrates and displaces in a reciprocating manner, so as to make the air flow through the at least one vacant space into the airflow chamber and achieve air transportation.

18. The actuation-and-detecting module according to claim 17, wherein the actuation element comprises:

a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to bend and vibrate in the reciprocating manner by the applied voltage.

19. The actuation-and-detecting module according to claim 18, wherein the adjusting resonance plate is thicker than the piezoelectric carrying plate.

20. An actuation-and-detecting module comprising:

at least one main body comprising a plurality of compartments, wherein the plurality of compartments comprises:

at least one first compartment having at least one first chamber, at least one second chamber, at least one first partition, at least one first inlet and at least one first outlet, wherein space inside the first compartment is divided into the first chamber and the second chamber by the first partition, the first inlet is in fluid communication with the first chamber, the first outlet is in fluid communication with the second chamber, and the first partition has at least one first communication opening in fluid communication with the first chamber and the second chamber;

at least one second compartment integrally combined with the first compartment, and having at least one third chamber and at least one gas through hole, wherein space inside the second compartment is defined as the third chamber, and the gas through hole is in fluid communication with the third chamber; and at least one third compartment integrally combined with the first compartment and the second compartment, and having at least one fourth chamber, at least one fifth chamber, at least one carrying partition, at least one second inlet and at least one second outlet, wherein space inside the third compartment is divided into the fourth chamber and the fifth chamber by the carrying partition, the second inlet is in fluid communication with the fourth chamber, the second outlet is in fluid communication with the fifth chamber, and the carrying partition has at least one second communication opening in fluid communication with the fourth chamber and the fifth chamber;

at least one fine particle detecting base disposed between the fourth chamber and the carrying partition of the third compartment and having at least one detecting channel and at least one receiving slot, wherein the receiving slot is disposed in one end of the detecting channel and in fluid communication with the detecting channel;

a plurality of actuator comprising:
  at least one first actuator disposed between the first partition and the first compartment in the second chamber to allow air to flow into the first chamber through the first inlet, be transported to the second chamber through the first communication opening and be discharged out through the first outlet, so as to achieve air transportation of the first compartment in one way; and
  at least one second actuator disposed within the receiving slot of the fine particle detecting base and sealing one end of the detecting channel to allow air to flow into the fourth chamber through the second inlet, be transported to the fifth chamber through the second communication opening, and be discharged out through the second outlet, so as to achieve air transportation of the third compartment in one way; and a plurality of sensors comprising:
  at least one first sensor disposed within the first chamber and spaced apart from the first actuator to monitor the air flowing through a surface thereof;
  at least one second sensor disposed with in the third chamber to monitor the air flowing into the third chamber; and
  at least one third sensor disposed on the carrying partition and located within the detecting channel of the fine particle detecting base to monitor the air flowing into the detecting channel.

* * * * *